US009146242B2

(12) United States Patent
Dillon et al.

(10) Patent No.: US 9,146,242 B2
(45) Date of Patent: Sep. 29, 2015

(54) LEVELS OF BLYS/APRIL HETEROTRIMERS IN SERUM AND USE IN DIAGNOSTIC METHODS

(71) Applicant: ZymoGenetics, Inc., Seattle, WA (US)

(72) Inventors: Stacey R. Dillon, Seattle, WA (US); Brandon J. Harder, Renton, WA (US)

(73) Assignee: ZymoGenetics, Inc., Seattle, WA (US)

( * ) Notice: Subject to any disclaimer, the term of this patent is extended or adjusted under 35 U.S.C. 154(b) by 45 days.

(21) Appl. No.: 13/972,186

(22) Filed: Aug. 21, 2013

(65) Prior Publication Data

US 2013/0330339 A1    Dec. 12, 2013

Related U.S. Application Data

(62) Division of application No. 12/428,146, filed on Apr. 22, 2009.

(60) Provisional application No. 61/049,706, filed on May 1, 2008.

(51) Int. Cl.
*G01N 33/68* (2006.01)
*G01N 33/564* (2006.01)

(52) U.S. Cl.
CPC .......... *G01N 33/6893* (2013.01); *G01N 33/564* (2013.01); *G01N 33/6863* (2013.01); *G01N 2333/70575* (2013.01); *G01N 2333/70578* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2004/0038349 A1 | 2/2004 | Hilbert et al. | |
| 2006/0034852 A1 | 2/2006 | Rixon et al. | |
| 2007/0086979 A1* | 4/2007 | Chevrier et al. | 424/85.1 |
| 2009/0291080 A1 | 11/2009 | Gottenberg et al. | |

FOREIGN PATENT DOCUMENTS

| | | |
|---|---|---|
| JP | 2004-537290 A | 12/2004 |
| WO | WO 02/02641 A1 | 1/2002 |
| WO | WO 02/16312 A2 | 2/2002 |
| WO | WO 02/094192 A2 | 11/2002 |
| WO | WO 03/035846 A2 | 5/2003 |
| WO | WO 2005/000351 A2 | 1/2005 |
| WO | WO 2007/030803 A2 | 3/2007 |
| WO | WO 2007/142667 A2 | 12/2007 |
| WO | WO 2008/009705 A1 | 1/2008 |

OTHER PUBLICATIONS

Baker, Kevin P., et al., "Generation and Characterization of LymphoStat-B, a Human Monoclonal Antibody that Antagonizes the Bioactivities of B Lymphocyte Stimulator," *Arthritis & Rheumatism*, vol. 48, No. 11, Nov. 2003, pp. 3253-3265.

Dillon, Stacey R., et al., "An APRIL to Remember: Novel TNF Ligands as Therapeutic Targets," *Nature Reviews*, vol. 5, Mar. 2006, pp. 235-246.
Matsushita, Takashi et al., "Elevated Serum APRIL Levels in Patients with Systemic Sclerosis: Distinct Profiles of Systemic Sclerosis Categorized by APRIL and BAFF," *The Journal of Rheumatology*, vol. 34, No. 10, (2007), pp. 2056-2062.
Matsushita, Takashi et al., "Elevated Serum Levels of APRIL, but not BAFF, in Patients with Atopic Dermatitis," *Experimental Dermatology*, vol. 17, 2007, pp. 197-202.
Roschke, Viktor et al., "BLyS and APRIL Form Biologically Active Heterotrimers that are Expressed in Patients with Systemic Immune-Based Rheumatic Diseases," *The Journal of Immunology*, vol. 169, 2002, pp. 4314-4321.
Tan, Soon-Min, et al., "Local Production of B Lymphocyte Stimulator Protein APRIL in Arthritic Joints of Patients with Inflammatory Arthritis," *Arthritis & Rheumatism*, vol. 48, No. 4, Apr. 2003, pp. 982, 992.
Thompson, Jeffrey S., et al., "BAFF-R, A Newly Identified TNF Receptor that Specifically Interacts with BAFF," *Science*, vol. 293, 2001, pp. 2108-2111.
Watanabe, R., et al., "Increased Serum Levels of a Proliferation-Inducing Ligand in Patents with Bullous Pemphigoid," *Journal of Dermatological Science*, vol. 46, 2007, pp. 53-60.
Jonsson, Marlin V., et al., "Association Between Circulating Levels of the Novel TNF Family Members APRIL and BAFF and Lymphoid Organization in Primary Sjö gren's Syndrome," *Journal of Clinical Immunology*, vol. 25, No. 3, May 2005, pp. 189-201.
Daridon, Capucine, et al., "BAFF, APRIL, TWE-PRIL: Who's Who?," *Autoimmunity Reviews*, vol. 7, 2008, pp. 267-271.
Seyler, Thorsten M., et al., "BLyS and APRIL in Rheumatoid Arthritis," *Journal of Clinical Investigation*, vol. 115, No. 11, Nov. 2005, pp. 3083-3092.
Zhang J., et al, "Cutting Edge: A Role for B Lymphocyte Stimulator in Systemic Lupus Erythematosus," *The Journal of Immunology*, vol. 166, Jan. 1, 2001, pp. 6-10.
Dario and Vignali, *Journal of Immunological Methods*, 2000; 243: 243-255.
Brown et al., *PNAS*, 2004; 101: 5518-5523.
Rutgers University websit regarding grammar and style at Rutgers. edu/~jlynch/Writing/a.html; used to discern proper usage of "a" and "an" with acronyms and the words beginning in "h", downloaded on Aug. 17, 2011.

(Continued)

*Primary Examiner* — Christina Borgeest
(74) *Attorney, Agent, or Firm* — Alston & Bird LLP

(57) ABSTRACT

The present invention provides a method of measuring the levels of BLyS/APRIL heterotrimers (HT) in a biological sample, in a preferred embodiment, in serum. The diagnostic assays are useful in predicting an individual's likelihood of developing or currently suffering from an autoimmune disease, such as SLE and for methods for treating an individual clinically diagnosed with an autoimmune disease. This diagnostic test serves to predict a patient's likelihood to respond to a specific drug treatment, in particular treatment with HT antagonists, either singly or in combination with other immune suppressive drugs.

10 Claims, 3 Drawing Sheets

(56) References Cited

OTHER PUBLICATIONS

Wells, *Biochemistry*, 1990, 29: 8509-8517.
NGO et al., "The Protein Folding Problem and Tertiary Structure Prediction," 1994, pp. 492-495.
Bork, *Genome Research*, 2000, 10: 398-400.
Skolnick et al., *Trends in Biotech.*, 2000, 18(1): 34-39.
Doerks et al., *Trends in Genetics*, 1998, 14: 248-250.
Smith et al., *Nature Biotechnology*, 1997, 15: 1222-1223.
Brenner, *Trends in Genetics*, 1999,15: 132-133.
Bork et al., *Trends in Genetics*, 1996, 12: 425-427.
Dillon et al., *Arthritis Research & Therapy*, 2010, 12: R48; 14 pages total.
Stohl, *Arthritis Research & Therapy*, 2010; 12: 111, 2 pages total.
Cheema et al., *Arthritis & Rheumatism*, 2001; 44: 1313-1319.
Vallerskog et al., *Arthritis Research & Therapy*, 2006; 8: R167; 10 pages total.
Gross et al., *Nature*, 2000; 404: 995/999.
Tak, P.O., et al., "Atacicept in Patients with Rhuematoid Arthritis: Results of a Multicenter, Phase Ib, Double-Blind, Placebo-Controlled, Dose-Escalating, Single-and Repeated-Dose Study," *Arthritis and Rheumatism*, Jan. 2008, vol. 58, No. 1, 61-72.

\* cited by examiner

SEQUENCE LISTING

<160> NUMBER OF SEQ ID NOS: 26

<210> SEQ ID NO 1
<211> LENGTH: 1377
<212> TYPE: DNA
<213> ORGANISM: homo sapiens
<220> FEATURE:
<221> NAME/KEY: CDS
<222> LOCATION: (14)...(892)

<400> SEQUENCE: 1

```
agcatcctga gta atg agt ggc ctg ggc cgg agc agg cga ggt ggc cgg          49
            Met Ser Gly Leu Gly Arg Ser Arg Arg Gly Gly Arg
                 1               5                  10 agc cgt gtg gac cag gag gag cgc ttt cca cag ggc ctg tgg acg ggg         97
Ser Arg Val Asp Gln Glu Glu Arg Phe Pro Gln Gly Leu Trp Thr Gly
```

```
                    15                   20                     25
gtg gct atg aga tcc tgc ccc gaa gag cag tac tgg gat cct ctg ctg    145
Val Ala Met Arg Ser Cys Pro Glu Glu Gln Tyr Trp Asp Pro Leu Leu
     30                  35                  40 ggt acc tgc atg tcc tgc aaa acc att tgc aac cat cag agc cag cgc    193
Gly Thr Cys Met Ser Cys Lys Thr Ile Cys Asn His Gln Ser Gln Arg
 45                  50                  55                  60 acc tgt gca gcc ttc tgc agg tca ctc agc tgc cgc aag gag caa ggc    241
Thr Cys Ala Ala Phe Cys Arg Ser Leu Ser Cys Arg Lys Glu Gln Gly
                 65                  70                  75 aag ttc tat gac cat ctc ctg agg gac tgc atc agc tgt gcc tcc atc    289
Lys Phe Tyr Asp His Leu Leu Arg Asp Cys Ile Ser Cys Ala Ser Ile
             80                  85                  90 tgt gga cag cac cct aag caa tgt gca tac ttc tgt gag aac aag ctc    337
Cys Gly Gln His Pro Lys Gln Cys Ala Tyr Phe Cys Glu Asn Lys Leu
         95                 100                 105 agg agc cca gtg aac ctt cca cca gag ctc agg aga cag cgg agt gga    385
Arg Ser Pro Val Asn Leu Pro Pro Glu Leu Arg Arg Gln Arg Ser Gly
    110                 115                 120 gaa gtt gaa aac aat tca gac aac tcg gga agg tac caa gga ttg gag    433
Glu Val Glu Asn Asn Ser Asp Asn Ser Gly Arg Tyr Gln Gly Leu Glu
125                 130                 135                 140 cac aga ggc tca gaa gca agt cca gct ctc ccg ggg ctg aag ctg agt    481
His Arg Gly Ser Glu Ala Ser Pro Ala Leu Pro Gly Leu Lys Leu Ser
                145                 150                 155 gca gat cag gtg gcc ctg gtc tac agc acg ctg ggg ctc tgc ctg tgt    529
Ala Asp Gln Val Ala Leu Val Tyr Ser Thr Leu Gly Leu Cys Leu Cys
            160                 165                 170 gcc gtc ctc tgc tgc ttc ctg gtg gcg gtg gcc tgc ttc ctc aag aag    577
Ala Val Leu Cys Cys Phe Leu Val Ala Val Ala Cys Phe Leu Lys Lys
        175                 180                 185 agg ggg gat ccc tgc tcc tgc cag ccc cgc tca agg ccc cgt caa agt    625
Arg Gly Asp Pro Cys Ser Cys Gln Pro Arg Ser Arg Pro Arg Gln Ser
    190                 195                 200 ccg gcc aag tct tcc cag gat cac gcg atg gaa gcc ggc agc cct gtg    673
Pro Ala Lys Ser Ser Gln Asp His Ala Met Glu Ala Gly Ser Pro Val
205                 210                 215                 220 agc aca tcc ccc gag cca gtg gag acc tgc agc ttc tgc ttc cct gag    721
Ser Thr Ser Pro Glu Pro Val Glu Thr Cys Ser Phe Cys Phe Pro Glu
                225                 230                 235 tgc agg gcg ccc acg cag gag agc gca gtc acg cct ggg acc ccc gac    769
Cys Arg Ala Pro Thr Gln Glu Ser Ala Val Thr Pro Gly Thr Pro Asp
            240                 245                 250 ccc act tgt gct gga agg tgg ggg tgc cac acc agg acc aca gtc ctg    817
Pro Thr Cys Ala Gly Arg Trp Gly Cys His Thr Arg Thr Thr Val Leu
        255                 260                 265 cag cct tgc cca cac atc cca gac agt ggc ctt ggc att gtg tgt gtg    865
Gln Pro Cys Pro His Ile Pro Asp Ser Gly Leu Gly Ile Val Cys Val
    270                 275                 280 cct gcc cag gag ggg ggc cca ggt gca taaatggggg tcagggaggg           912
Pro Ala Gln Glu Gly Gly Pro Gly Ala
285                 290 aaaggaggag ggagagagat ggagaggagg ggagagagaa agagaggtgg ggagagggga    972
gagagatatg aggagagaga gacagaggag gcagaaaggg agagaaacag aggagacaga   1032
gagggagaga gagacagagg gagagagaga cagaggggaa gagaggcaga gagggaaaga   1092
ggcagagaag gaaagagaca ggcagagaag gagagaggca gagagggaga gaggcagaga   1152
gggagagagg cagagagaca gagagggaga gagggacaga gagagataga gcaggaggtc   1212
```

-continued

```
ggggcactct gagtcccagt tcccagtgca gctgtaggtc gtcatccct  aaccacacgt  1272 gcaataaagt cctcgtgcct gctgctcaca gcccccgaga gccctcctc  ctggagaata  1332 aaacctttgg cagctgccct tcctcaaaaa aaaaaaaaaa aaaaa                 1377
```

<210> SEQ ID NO 2
<211> LENGTH: 293
<212> TYPE: PRT
<213> ORGANISM: homo sapiens

<400> SEQUENCE: 2

```
Met Ser Gly Leu Gly Arg Ser Arg Gly Gly Arg Ser Arg Val Asp
 1               5                  10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290
```

<210> SEQ ID NO 3
<211> LENGTH: 586
<212> TYPE: DNA
<213> ORGANISM: homo sapiens
<220> FEATURE:
<221> NAME/KEY: CDS

<222> LOCATION: (27)...(578)

<400> SEQUENCE: 3

```
gcagcttgtg cggcggcgtc ggcacc atg agg cga ggg ccc cgg agc ctg cgg         53
                              Met Arg Arg Gly Pro Arg Ser Leu Arg
                               1               5 ggc agg gac gcg cca gcc ccc acg ccc tgc gtc ccg gcc gag tgc ttc         101
Gly Arg Asp Ala Pro Ala Pro Thr Pro Cys Val Pro Ala Glu Cys Phe
 10                  15                  20                  25 gac ctg ctg gtc cgc cac tgc gtg gcc tgc ggg ctc ctg cgc acg ccg         149
Asp Leu Leu Val Arg His Cys Val Ala Cys Gly Leu Leu Arg Thr Pro
                 30                  35                  40 cgg ccg aaa ccg gcc ggg gcc agc agc cct gcg ccc agg acg gcg ctg         197
Arg Pro Lys Pro Ala Gly Ala Ser Ser Pro Ala Pro Arg Thr Ala Leu
             45                  50                  55 cag ccg cag gag tcg gtg ggc gcg ggc gcc ggc gag gcg gcg ctg ccc         245
Gln Pro Gln Glu Ser Val Gly Ala Gly Ala Gly Glu Ala Ala Leu Pro
         60                  65                  70 ctg ccc ggg ctg ctc ttt ggc gcc ccc gcg ctg ggc ctg gca ctg             293
Leu Pro Gly Leu Leu Phe Gly Ala Pro Ala Leu Leu Gly Leu Ala Leu
     75                  80                  85 gtc ctg gcg ctg gtc ctg gtg ggt ctg gtg agc tgg agg cgg cga cag         341
Val Leu Ala Leu Val Leu Val Gly Leu Val Ser Trp Arg Arg Arg Gln
 90                  95                 100                 105 cgg cgg ctt cgc ggc gcg tcc tcc gca gag gcc ccc gac gga gac aag         389
Arg Arg Leu Arg Gly Ala Ser Ser Ala Glu Ala Pro Asp Gly Asp Lys
                 110                 115                 120 gac gcc cca gag ccc ctg gac aag gtc atc att ctg tct ccg gga atc         437
Asp Ala Pro Glu Pro Leu Asp Lys Val Ile Ile Leu Ser Pro Gly Ile
             125                 130                 135 tct gat gcc aca gct cct gcc tgg cct cct cct ggg gaa gac cca gga         485
Ser Asp Ala Thr Ala Pro Ala Trp Pro Pro Pro Gly Glu Asp Pro Gly
         140                 145                 150 acc acc cca cct ggc cac agt gtc cct gtg cca gcc aca gag ctg ggc         533
Thr Thr Pro Pro Gly His Ser Val Pro Val Pro Ala Thr Glu Leu Gly
     155                 160                 165 tcc act gaa ctg gtg acc acc aag acg gcc ggc cct gag caa caa             578
Ser Thr Glu Leu Val Thr Thr Lys Thr Ala Gly Pro Glu Gln Gln
170                 175                 180 tagcaggg                                                                586
```

<210> SEQ ID NO 4
<211> LENGTH: 184
<212> TYPE: PRT
<213> ORGANISM: homo sapiens

<400> SEQUENCE: 4

```
Met Arg Arg Gly Pro Arg Ser Leu Arg Gly Arg Asp Ala Pro Ala Pro
 1               5                  10                  15

Thr Pro Cys Val Pro Ala Glu Cys Phe Asp Leu Leu Val Arg His Cys
             20                  25                  30

Val Ala Cys Gly Leu Leu Arg Thr Pro Arg Pro Lys Pro Ala Gly Ala
         35                  40                  45

Ser Ser Pro Ala Pro Arg Thr Ala Leu Gln Pro Gln Glu Ser Val Gly
     50                  55                  60

Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
             85                  90                  95
```

```
Gly Leu Val Ser Trp Arg Arg Gln Arg Leu Arg Gly Ala Ser
            100                 105                 110
Ser Ala Glu Ala Pro Asp Gly Lys Asp Ala Pro Glu Pro Leu Asp
            115                 120                 125
Lys Val Ile Ile Leu Ser Pro Gly Ile Ser Asp Ala Thr Ala Pro Ala
            130                 135                 140
Trp Pro Pro Pro Gly Glu Asp Pro Gly Thr Thr Pro Pro Gly His Ser
145                 150                 155                 160
Val Pro Val Pro Ala Thr Glu Leu Gly Ser Thr Glu Leu Val Thr Thr
                    165                 170                 175
Lys Thr Ala Gly Pro Glu Gln Gln
            180

<210> SEQ ID NO 5
<211> LENGTH: 995
<212> TYPE: DNA
<213> ORGANISM: homo sapiens
<220> FEATURE:
<221> NAME/KEY: CDS
<222> LOCATION: (219)...(770)

<400> SEQUENCE: 5
aagactcaaa cttagaaact tgaattagat gtggtattca atccttacg tgccgcgaag      60 acacagacag cccccgtaag aacccacgaa gcaggcgaag ttcattgttc tcaacattct     120
agctgctctt gctgcatttg ctctggaatt cttgtagaga tattacttgt ccttccaggc    180
tgttctttct gtagctccct gttttctttt tgtgatc atg ttg cag atg gct ggg     236
                                        Met Leu Gln Met Ala Gly
                                        1               5 cag tgc tcc caa aat gaa tat ttt gac agt ttg ttg cat gct tgc ata      284
Gln Cys Ser Gln Asn Glu Tyr Phe Asp Ser Leu Leu His Ala Cys Ile
            10                  15                  20 cct tgt caa ctt cga tgt tct tct aat act cct cct cta aca tgt cag     332
Pro Cys Gln Leu Arg Cys Ser Ser Asn Thr Pro Pro Leu Thr Cys Gln
        25                  30                  35 cgt tat tgt aat gca agt gtg acc aat tca gtg aaa gga acg aat gcg     380
Arg Tyr Cys Asn Ala Ser Val Thr Asn Ser Val Lys Gly Thr Asn Ala
    40                  45                  50 att ctc tgg acc tgt ttg gga ctg agc tta ata att tct ttg gca gtt     428
Ile Leu Trp Thr Cys Leu Gly Leu Ser Leu Ile Ile Ser Leu Ala Val
55                  60                  65                  70 ttc gtg cta atg ttt ttg cta agg aag ata agc tct gaa cca tta aag     476
Phe Val Leu Met Phe Leu Leu Arg Lys Ile Ser Ser Glu Pro Leu Lys
                75                  80                  85 gac gag ttt aaa aac aca gga tca ggt ctc ctg ggc atg gct aac att     524
Asp Glu Phe Lys Asn Thr Gly Ser Gly Leu Leu Gly Met Ala Asn Ile
            90                  95                  100 gac ctg gaa aag agc agg act ggt gat gaa att att ctt ccg aga ggc     572
Asp Leu Glu Lys Ser Arg Thr Gly Asp Glu Ile Ile Leu Pro Arg Gly
        105                 110                 115 ctc gag tac acg gtg gaa gaa tgc acc tgt gaa gac tgc atc aag agc     620
Leu Glu Tyr Thr Val Glu Glu Cys Thr Cys Glu Asp Cys Ile Lys Ser
    120                 125                 130 aaa ccg aag gtc gac tct gac cat tgc ttt cca ctc cca gct atg gag     668
Lys Pro Lys Val Asp Ser Asp His Cys Phe Pro Leu Pro Ala Met Glu
135                 140                 145                 150 gaa ggc gca acc att ctt gtc acc acg aaa acg aat gac tat tgc aag     716
Glu Gly Ala Thr Ile Leu Val Thr Thr Lys Thr Asn Asp Tyr Cys Lys
                155                 160                 165
```

| | | | | | | | | | | | | | | |
|---|---|---|---|---|---|---|---|---|---|---|---|---|---|---|
| agc | ctg | cca | gct | gct | ttg | agt | gct | acg | gag | ata | gag | aaa | tca | att tct | 764
| Ser | Leu | Pro | Ala | Ala | Leu | Ser | Ala | Thr | Glu | Ile | Glu | Lys | Ser | Ile Ser |
| | | 170 | | | | 175 | | | | 180 | | | | | gct agg taattaacca tttcgactcg agcagtgcca ctttaaaaat cttttgtcag   820
Ala Arg aatagatgat gtgtcagatc tctttaggat gactgtattt ttcagttgcc gatacagctt   880
tttgtcctct aactgtggaa actctttatg ttagatatat ttctctaggt tactgttggg   940
agcttaatgg tagaaacttc cttggtttca tgattaaagt cttttttttt cctga   995

<210> SEQ ID NO 6
<211> LENGTH: 184
<212> TYPE: PRT
<213> ORGANISM: homo sapiens

<400> SEQUENCE: 6

Met Leu Gln Met Ala Gly Gln Cys Ser Gln Asn Glu Tyr Phe Asp Ser
 1               5                  10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 7
<211> LENGTH: 1149
<212> TYPE: DNA
<213> ORGANISM: homo sapiens
<220> FEATURE:
<221> NAME/KEY: CDS
<222> LOCATION: (173)...(1023)

<400> SEQUENCE: 7
gaattcggca cgaggcagaa aggagaaaat tcaggataac tctcctgagg ggtgagccaa   60
gccctgccat gtagtgcacg caggacatca acaaacacag ataacaggaa atgatccatt   120
ccctgtggtc acttattcta aaggccccaa ccttcaaagt tcaagtagtg at atg gat   178
                                                        Met Asp
                                                          1

| | | | | | | | | | | | | | | |
|---|---|---|---|---|---|---|---|---|---|---|---|---|---|---|
| gac | tcc | aca | gaa | agg | gag | cag | tca | cgc | ctt | act | tct | tgc | ctt | aag aaa | 226
| Asp | Ser | Thr | Glu | Arg | Glu | Gln | Ser | Arg | Leu | Thr | Ser | Cys | Leu | Lys Lys |

|    |    |    |    |    |    |    |    |    |    |    |    |    |    |    |    |      |
|----|----|----|----|----|----|----|----|----|----|----|----|----|----|----|----|------|
|    |    |    |    | 5  |    |    |    |    | 10 |    |    |    |    | 15 |    |      |
| aga | gaa | gaa | atg | aaa | ctg | aag | gag | tgt | gtt | tcc | atc | ctc | cca | cgg | aag | 274  |
| Arg | Glu | Glu | Met | Lys | Leu | Lys | Glu | Cys | Val | Ser | Ile | Leu | Pro | Arg | Lys |      |
|    | 20  |    |    |    |    | 25  |    |    |    |    | 30  |    |    |    |    |      |
| gaa | agc | ccc | tct | gtc | cga | tcc | tcc | aaa | gac | gga | aag | ctg | ctg | gct | gca | 322  |
| Glu | Ser | Pro | Ser | Val | Arg | Ser | Ser | Lys | Asp | Gly | Lys | Leu | Leu | Ala | Ala |      |
| 35 |    |    |    |    | 40 |    |    |    |    | 45 |    |    |    |    | 50 |      |
| acc | ttg | ctg | ctg | gca | ctg | ctg | tct | tgc | tgc | ctc | acg | gtg | gtg | tct | ttc | 370  |
| Thr | Leu | Leu | Leu | Ala | Leu | Leu | Ser | Cys | Cys | Leu | Thr | Val | Val | Ser | Phe |      |
|    |    |    |    | 55 |    |    |    |    | 60 |    |    |    |    | 65 |    |      |
| tac | cag | gtg | gcc | gcc | ctg | caa | ggg | gac | ctg | gcc | agc | ctc | cgg | gca | gag | 418  |
| Tyr | Gln | Val | Ala | Ala | Leu | Gln | Gly | Asp | Leu | Ala | Ser | Leu | Arg | Ala | Glu |      |
|    |    |    | 70 |    |    |    |    | 75 |    |    |    |    | 80 |    |    |      |
| ctg | cag | ggc | cac | cac | gcg | gag | aag | ctg | cca | gca | gga | gca | gga | gcc | ccc | 466  |
| Leu | Gln | Gly | His | His | Ala | Glu | Lys | Leu | Pro | Ala | Gly | Ala | Gly | Ala | Pro |      |
|    |    | 85 |    |    |    |    | 90 |    |    |    |    | 95 |    |    |    |      |
| aag | gcc | ggc | ctg | gag | gaa | gct | cca | gct | gtc | acc | gcg | gga | ctg | aaa | atc | 514  |
| Lys | Ala | Gly | Leu | Glu | Glu | Ala | Pro | Ala | Val | Thr | Ala | Gly | Leu | Lys | Ile |      |
|    | 100 |    |    |    |    | 105 |    |    |    |    | 110 |    |    |    |    |      |
| ttt | gaa | cca | cca | gct | cca | gga | gaa | ggc | aac | tcc | agt | cag | aac | agc | aga | 562  |
| Phe | Glu | Pro | Pro | Ala | Pro | Gly | Glu | Gly | Asn | Ser | Ser | Gln | Asn | Ser | Arg |      |
| 115 |    |    |    |    | 120 |    |    |    |    | 125 |    |    |    |    | 130 |      |
| aat | aag | cgt | gcc | gtt | cag | ggt | cca | gaa | gaa | aca | gtc | act | caa | gac | tgc | 610  |
| Asn | Lys | Arg | Ala | Val | Gln | Gly | Pro | Glu | Glu | Thr | Val | Thr | Gln | Asp | Cys |      |
|    |    |    | 135 |    |    |    |    | 140 |    |    |    |    | 145 |    |    |      |
| ttg | caa | ctg | att | gca | gac | agt | gaa | aca | cca | act | ata | caa | aaa | gga | tct | 658  |
| Leu | Gln | Leu | Ile | Ala | Asp | Ser | Glu | Thr | Pro | Thr | Ile | Gln | Lys | Gly | Ser |      |
|    |    | 150 |    |    |    |    | 155 |    |    |    |    | 160 |    |    |    |      |
| tac | aca | ttt | gtt | cca | tgg | ctt | ctc | agc | ttt | aaa | agg | gga | agt | gcc | cta | 706  |
| Tyr | Thr | Phe | Val | Pro | Trp | Leu | Leu | Ser | Phe | Lys | Arg | Gly | Ser | Ala | Leu |      |
|    | 165 |    |    |    |    | 170 |    |    |    |    | 175 |    |    |    |    |      |
| gaa | gaa | aaa | gag | aat | aaa | ata | ttg | gtc | aaa | gaa | act | ggt | tac | ttt | ttt | 754  |
| Glu | Glu | Lys | Glu | Asn | Lys | Ile | Leu | Val | Lys | Glu | Thr | Gly | Tyr | Phe | Phe |      |
| 180 |    |    |    |    | 185 |    |    |    |    | 190 |    |    |    |    |    |      |
| ata | tat | ggt | cag | gtt | tta | tat | act | gat | aag | acc | tac | gcc | atg | gga | cat | 802  |
| Ile | Tyr | Gly | Gln | Val | Leu | Tyr | Thr | Asp | Lys | Thr | Tyr | Ala | Met | Gly | His |      |
| 195 |    |    |    |    | 200 |    |    |    |    | 205 |    |    |    |    | 210 |      |
| cta | att | cag | agg | aag | aag | gtc | cat | gtc | ttt | ggg | gat | gaa | ttg | agt | ctg | 850  |
| Leu | Ile | Gln | Arg | Lys | Lys | Val | His | Val | Phe | Gly | Asp | Glu | Leu | Ser | Leu |      |
|    |    |    |    | 215 |    |    |    |    | 220 |    |    |    |    | 225 |    |      |
| gtg | act | ttg | ttt | cga | tgt | att | caa | aat | atg | cct | gaa | aca | cta | ccc | aat | 898  |
| Val | Thr | Leu | Phe | Arg | Cys | Ile | Gln | Asn | Met | Pro | Glu | Thr | Leu | Pro | Asn |      |
|    |    |    | 230 |    |    |    |    | 235 |    |    |    |    | 240 |    |    |      |
| aat | tcc | tgc | tat | tca | gct | ggc | att | gca | aaa | ctg | gaa | gaa | gga | gat | gaa | 946  |
| Asn | Ser | Cys | Tyr | Ser | Ala | Gly | Ile | Ala | Lys | Leu | Glu | Glu | Gly | Asp | Glu |      |
|    |    | 245 |    |    |    |    | 250 |    |    |    |    | 255 |    |    |    |      |
| ctc | caa | ctt | gca | ata | cca | aga | gaa | aat | gca | caa | ata | tca | ctg | gat | gga | 994  |
| Leu | Gln | Leu | Ala | Ile | Pro | Arg | Glu | Asn | Ala | Gln | Ile | Ser | Leu | Asp | Gly |      |
|    | 260 |    |    |    |    | 265 |    |    |    |    | 270 |    |    |    |    |      |
| gat | gtc | aca | ttt | ttt | ggt | gca | ttg | aaa | ct gctgtgacct acttacacca | | | | | | | 1043 |
| Asp | Val | Thr | Phe | Phe | Gly | Ala | Leu | Lys |    |    |    |    |    |    |    |      |
| 275 |    |    |    |    | 280 |    |    |    |    |    |    |    |    |    |    |      | tgtctgtagc tattttcctc cctttctctg tacctctaag aagaaagaat ctaactgaaa    1103 ataccaaaaa aaaaaaaaaa aaaaaaaaaa ccctcgagcg gccgcc    1149

<210> SEQ ID NO 8
<211> LENGTH: 283
<212> TYPE: PRT
<213> ORGANISM: homo sapiens

<400> SEQUENCE: 8

```
Met Asp Asp Ser Thr Glu Arg Glu Gln Ser Arg Leu Thr Ser Cys Leu
 1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
 50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys
        275                 280
```

<210> SEQ ID NO 9
<211> LENGTH: 185
<212> TYPE: PRT
<213> ORGANISM: homo sapiens

<400> SEQUENCE: 9

```
Met Arg Arg Gly Pro Arg Ser Leu Arg Gly Arg Asp Ala Pro Ala Pro
 1               5                  10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ala Ser Ser Pro Ala Pro Arg Thr Ala Leu Gln Pro Gln Glu Ser Val
 50                  55                  60

Gly Ala Gly Ala Gly Glu Ala Ala Leu Pro Leu Pro Gly Leu Leu Phe
 65                  70                  75                  80
```

```
Gly Ala Pro Ala Leu Leu Gly Leu Ala Leu Val Leu Ala Leu Val Leu
                85                  90                  95

Val Gly Leu Val Ser Trp Arg Arg Gln Arg Arg Leu Arg Gly Ala
            100                 105                 110

Ser Ser Ala Glu Ala Pro Asp Gly Asp Lys Asp Ala Pro Glu Pro Leu
            115                 120                 125

Asp Lys Val Ile Ile Leu Ser Pro Gly Ile Ser Asp Ala Thr Ala Pro
130                 135                 140

Ala Trp Pro Pro Pro Gly Glu Asp Pro Gly Thr Thr Pro Pro Gly His
145                 150                 155                 160

Ser Val Pro Val Pro Ala Thr Glu Leu Gly Ser Thr Glu Leu Val Thr
                165                 170                 175

Thr Lys Thr Ala Gly Pro Glu Gln Gln
                180                 185

<210> SEQ ID NO 10
<211> LENGTH: 247
<212> TYPE: PRT
<213> ORGANISM: homo sapiens

<400> SEQUENCE: 10

Met Ser Gly Leu Gly Arg Ser Arg Arg Gly Gly Arg Ser Arg Val Asp
1               5                   10                  15

Gln Glu Glu Arg Trp Ser Leu Ser Cys Arg Lys Glu Gln Gly Lys Phe
            20                  25                  30

Tyr Asp His Leu Leu Arg Asp Cys Ile Ser Cys Ala Ser Ile Cys Gly
        35                  40                  45

Gln His Pro Lys Gln Cys Ala Tyr Phe Cys Glu Asn Lys Leu Arg Ser
    50                  55                  60

Pro Val Asn Leu Pro Pro Glu Leu Arg Arg Gln Arg Ser Gly Glu Val
65                  70                  75                  80

Glu Asn Asn Ser Asp Asn Ser Gly Arg Tyr Gln Gly Leu Glu His Arg
                85                  90                  95

Gly Ser Glu Ala Ser Pro Ala Leu Pro Gly Leu Lys Leu Ser Ala Asp
            100                 105                 110

Gln Val Ala Leu Val Tyr Ser Thr Leu Gly Leu Cys Leu Cys Ala Val
        115                 120                 125

Leu Cys Cys Phe Leu Val Ala Val Ala Cys Phe Leu Lys Lys Arg Gly
130                 135                 140

Asp Pro Cys Ser Cys Gln Pro Arg Ser Arg Pro Arg Gln Ser Pro Ala
145                 150                 155                 160

Lys Ser Ser Gln Asp His Ala Met Glu Ala Gly Ser Pro Val Ser Thr
                165                 170                 175

Ser Pro Glu Pro Val Glu Thr Cys Ser Phe Cys Phe Pro Glu Cys Arg
            180                 185                 190

Ala Pro Thr Gln Glu Ser Ala Val Thr Pro Gly Thr Pro Asp Pro Thr
        195                 200                 205

Cys Ala Gly Arg Trp Gly Cys His Thr Arg Thr Thr Val Leu Gln Pro
210                 215                 220

Cys Pro His Ile Pro Asp Ser Gly Leu Gly Ile Val Cys Val Pro Ala
225                 230                 235                 240

Gln Glu Gly Gly Pro Gly Ala
                245
```

```
<210> SEQ ID NO 11
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 11

Glu Cys Phe Asp Leu Leu Val Arg Ala Trp Val Pro Cys Ser Val Leu
 1               5                  10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 12

Glu Cys Phe Asp Leu Leu Val Arg Ala Trp Val Pro Cys Ser Val Leu
 1               5                  10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 13

Glu Cys Phe Asp Leu Leu Val Arg Arg Trp Val Pro Cys Glu Met Leu
 1               5                  10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 14

Glu Cys Phe Asp Leu Leu Val Arg Ser Trp Val Pro Cys His Met Leu
 1               5                  10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 15

Glu Cys Phe Asp Leu Leu Val Arg His Trp Val Ala Cys Gly Leu Leu
 1               5                  10                  15

Arg

<210> SEQ ID NO 16
<211> LENGTH: 1214
<212> TYPE: DNA
<213> ORGANISM: Artificial Sequence
```

```
<220> FEATURE:
<223> OTHER INFORMATION: TACI-Fc fusion protein
<220> FEATURE:
<221> NAME/KEY: CDS
<222> LOCATION: (17)...(1192)

<400> SEQUENCE: 16
tattaggccg gccacc atg gat gca atg aag aga ggg ctc tgc tgt gtg ctg          52
               Met Asp Ala Met Lys Arg Gly Leu Cys Cys Val Leu
                 1               5                  10 ctg ctg tgt ggc gcc gtc ttc gtt tcg ctc agc cag gaa atc cat gcc           100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag           148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc           196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc           244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc           292
Cys Arg Lys Glu Gln Gly Lys Phe Tyr Asp His Leu Leu Arg Asp Cys
             80                  85                  90 atc agc tgt gcc tcc atc tgt gga cag cac cct aag caa tgt gca tac           340
Ile Ser Cys Ala Ser Ile Cys Gly Gln His Pro Lys Gln Cys Ala Tyr
         95                 100                 105 ttc tgt gag aac aag ctc agg agc cca gtg aac ctt cca cca gag ctc           388
Phe Cys Glu Asn Lys Leu Arg Ser Pro Val Asn Leu Pro Pro Glu Leu
110                 115                 120 agg aga cag cgg agt gga gaa gtt gaa aac aat tca gac aac tcg gga           436
Arg Arg Gln Arg Ser Gly Glu Val Glu Asn Asn Ser Asp Asn Ser Gly
125                 130                 135                 140 agg tac caa gga ttg gag cac aga ggc tca gaa gca agt cca gct ctc           484
Arg Tyr Gln Gly Leu Glu His Arg Gly Ser Glu Ala Ser Pro Ala Leu
                145                 150                 155 cca ggt ctc aag gag ccc aaa tct tca gac aaa act cac aca tgc cca           532
Pro Gly Leu Lys Glu Pro Lys Ser Ser Asp Lys Thr His Thr Cys Pro
            160                 165                 170 ccg tgc cca gca cct gaa gcc gag ggg gca ccg tca gtc ttc ctc ttc           580
Pro Cys Pro Ala Pro Glu Ala Glu Gly Ala Pro Ser Val Phe Leu Phe
        175                 180                 185 ccc cca aaa ccc aag gac acc ctc atg atc tcc cgg acc cct gag gtc           628
Pro Pro Lys Pro Lys Asp Thr Leu Met Ile Ser Arg Thr Pro Glu Val
190                 195                 200 aca tgc gtg gtg gtg gac gtg agc cac gaa gac cct gag gtc aag ttc           676
Thr Cys Val Val Val Asp Val Ser His Glu Asp Pro Glu Val Lys Phe
205                 210                 215                 220 aac tgg tac gtg gac ggc gtg gag gtg cat aat gcc aag aca aag ccg           724
Asn Trp Tyr Val Asp Gly Val Glu Val His Asn Ala Lys Thr Lys Pro
                225                 230                 235 cgg gag gag cag tac aac agc acg tac cgt gtg gtc agc gtc ctc acc           772
Arg Glu Glu Gln Tyr Asn Ser Thr Tyr Arg Val Val Ser Val Leu Thr
            240                 245                 250 gtc ctg cac cag gac tgg ctg aat ggc aag gag tac aag tgc aag gtc           820
Val Leu His Gln Asp Trp Leu Asn Gly Lys Glu Tyr Lys Cys Lys Val
        255                 260                 265 tcc aac aaa gcc ctc cca tcc tcc atc gag aaa acc atc tcc aaa gcc           868
Ser Asn Lys Ala Leu Pro Ser Ser Ile Glu Lys Thr Ile Ser Lys Ala
270                 275                 280
```

```
aaa ggg cag ccc cga gaa cca cag gtg tac acc ctg ccc cca tcc cgg    916
Lys Gly Gln Pro Arg Glu Pro Gln Val Tyr Thr Leu Pro Pro Ser Arg
285                 290                 295                 300 gat gag ctg acc aag aac cag gtc agc ctg acc tgc ctg gtc aaa ggc    964
Asp Glu Leu Thr Lys Asn Gln Val Ser Leu Thr Cys Leu Val Lys Gly
                305                 310                 315 ttc tat ccc agc gac atc gcc gtg gag tgg gag agc aat ggg cag ccg   1012
Phe Tyr Pro Ser Asp Ile Ala Val Glu Trp Glu Ser Asn Gly Gln Pro
            320                 325                 330 gag aac aac tac aag acc acg cct ccc gtg ctg gac tcc gac ggc tcc   1060
Glu Asn Asn Tyr Lys Thr Thr Pro Pro Val Leu Asp Ser Asp Gly Ser
        335                 340                 345 ttc ttc ctc tac agc aag ctc acc gtg gac aag agc agg tgg cag cag   1108
Phe Phe Leu Tyr Ser Lys Leu Thr Val Asp Lys Ser Arg Trp Gln Gln
    350                 355                 360 ggg aac gtc ttc tca tgc tcc gtg atg cat gag gct ctg cac aac cac   1156
Gly Asn Val Phe Ser Cys Ser Val Met His Glu Ala Leu His Asn His
365                 370                 375                 380 tac acg cag aag agc ctc tcc ctg tct ccg ggt aaa taatctagag         1202
Tyr Thr Gln Lys Ser Leu Ser Leu Ser Pro Gly Lys
                385                 390 gcgcgccaat ta                                                     1214

<210> SEQ ID NO 17
<211> LENGTH: 392
<212> TYPE: PRT
<213> ORGANISM: Artificial Sequence
<220> FEATURE:
<223> OTHER INFORMATION: TACI-Fc fusion protein

<400> SEQUENCE: 17

Met Asp Ala Met Lys Arg Gly Leu Cys Cys Val Leu Leu Leu Cys Gly
  1               5                  10                  15

Ala Val Phe Val Ser Leu Ser Gln Glu Ile His Ala Glu Leu Arg Arg
                 20                  25                  30

Phe Arg Arg Ala Met Arg Ser Cys Pro Glu Glu Gln Tyr Trp Asp Pro
             35                  40                  45

Leu Leu Gly Thr Cys Met Ser Cys Lys Thr Ile Cys Asn His Gln Ser
         50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
                 85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Arg Gln Arg
        115                 120                 125

Ser Gly Glu Val Glu Asn Asn Ser Asp Asn Ser Gly Arg Tyr Gln Gly
    130                 135                 140

Leu Glu His Arg Gly Ser Glu Ala Ser Pro Ala Leu Pro Gly Leu Lys
145                 150                 155                 160

Glu Pro Lys Ser Ser Asp Lys Thr His Thr Cys Pro Pro Cys Pro Ala
                165                 170                 175

Pro Glu Ala Glu Gly Ala Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205
```

```
Val Asp Val Ser His Glu Asp Pro Glu Val Lys Phe Asn Trp Tyr Val
    210                 215                 220
Asp Gly Val Glu Val His Asn Ala Lys Thr Lys Pro Arg Glu Glu Gln
225                 230                 235                 240
Tyr Asn Ser Thr Tyr Arg Val Val Ser Val Leu Thr Val Leu His Gln
                245                 250                 255
Asp Trp Leu Asn Gly Lys Glu Tyr Lys Cys Lys Val Ser Asn Lys Ala
            260                 265                 270
Leu Pro Ser Ser Ile Glu Lys Thr Ile Ser Lys Ala Lys Gly Gln Pro
        275                 280                 285
Arg Glu Pro Gln Val Tyr Thr Leu Pro Pro Ser Arg Asp Glu Leu Thr
290                 295                 300
Lys Asn Gln Val Ser Leu Thr Cys Leu Val Lys Gly Phe Tyr Pro Ser
305                 310                 315                 320
Asp Ile Ala Val Glu Trp Glu Ser Asn Gly Gln Pro Glu Asn Asn Tyr
                325                 330                 335
Lys Thr Thr Pro Pro Val Leu Asp Ser Asp Gly Ser Phe Phe Leu Tyr
            340                 345                 350
Ser Lys Leu Thr Val Asp Lys Ser Arg Trp Gln Gln Gly Asn Val Phe
        355                 360                 365
Ser Cys Ser Val Met His Glu Ala Leu His Asn His Tyr Thr Gln Lys
370                 375                 380
Ser Leu Ser Leu Ser Pro Gly Lys
385                 390
```

<210> SEQ ID NO 18
<211> LENGTH: 1070
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1048)

<400> SEQUENCE: 18

```
tattaggccg gccacc atg gat gca atg aag aga ggg ctc tgc tgt gtg ctg    52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc    100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag    148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc    196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc    244
Asn His Gln Ser Gln Arg Thr Cys Ala Ala Phe Cys Arg Ser Leu Ser
                65                  70                  75 tgc cgc aag gag caa ggc aag ttc tat gac cat ctc ctg agg gac tgc    292
Cys Arg Lys Glu Gln Gly Lys Phe Tyr Asp His Leu Leu Arg Asp Cys
            80                  85                  90 atc agc tgt gcc tcc atc tgt gga cag cac cct aag caa tgt gca tac    340
Ile Ser Cys Ala Ser Ile Cys Gly Gln His Pro Lys Gln Cys Ala Tyr
        95                  100                 105 ttc tgt gag aac gag ccc aaa tct tca gac aaa act cac aca tgc cca    388
```

-continued

| | | |
|---|---|---|
| Phe Cys Glu Asn Glu Pro Lys Ser Ser Asp Lys Thr His Thr Cys Pro<br>110               115                   120 | | |
| ccg tgc cca gca cct gaa gcc gag ggg gca ccg tca gtc ttc ctc ttc<br>Pro Cys Pro Ala Pro Glu Ala Glu Gly Ala Pro Ser Val Phe Leu Phe<br>125               130                 135              140 | 436 | |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>               145                 150               155 | 484 | |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>160               165                   170 | 532 | |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>               175                 180               185 | 580 | |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>190               195                   200 | 628 | |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>205               210                 215              220 | 676 | |
| tcc aac aaa gcc ctc cca tcc tcc atc gag aaa acc atc tcc aaa gcc<br>Ser Asn Lys Ala Leu Pro Ser Ser Ile Glu Lys Thr Ile Ser Lys Ala<br>               225                 230               235 | 724 | |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>240               245                   250 | 772 | |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>255               260                   265 | 820 | |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>               270                 275               280 | 868 | |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>285               290                 295              300 | 916 | |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>               305                 310               315 | 964 | |
| ggg aac gtc ttc tca tgc tcc gtg atg cat gag gct ctg cac aac cac<br>Gly Asn Val Phe Ser Cys Ser Val Met His Glu Ala Leu His Asn His<br>320               325                 330 | 1012 | |
| tac acg cag aag agc ctc tcc ctg tct ccg ggt aaa taatctagag<br>Tyr Thr Gln Lys Ser Leu Ser Leu Ser Pro Gly Lys<br>               335                 340 | 1058 | |
| gcgcgccaat ta | 1070 | |

<210> SEQ ID NO 19
<211> LENGTH: 344
<212> TYPE: PRT
<213> ORGANISM: Artificial Sequence
<220> FEATURE:
<223> OTHER INFORMATION: TACI-Fc fusion protein

<400> SEQUENCE: 19

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

```
Leu Leu Gly Thr Cys Met Ser Cys Lys Thr Ile Cys Asn His Gln Ser
            50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Glu Pro Lys Ser Ser Asp Lys Thr His Thr Cys Pro Pro Cys Pro Ala
        115                 120                 125

Pro Glu Ala Glu Gly Ala Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 20
<211> LENGTH: 1082
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1060)

<400> SEQUENCE: 20
tattaggccg gccacc atg gat gca atg aag aga ggg ctc tgc tgt gtg ctg      52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc      100
Leu Leu Cys Gly Ala Val Phe Val Ser Leu Ser Gln Glu Ile His Ala
            15                  20                  25
```

```
gag ttg aga cgc ttc cgt aga gct atg aga tcc tgc ccc gaa gag cag      148
Glu Leu Arg Arg Phe Arg Arg Ala Met Arg Ser Cys Pro Glu Glu Gln
     30              35                  40 tac tgg gat cct ctg ctg ggt acc tgc atg tcc tgc aaa acc att tgc      196
Tyr Trp Asp Pro Leu Leu Gly Thr Cys Met Ser Cys Lys Thr Ile Cys
 45              50                  55                      60 aac cat cag agc cag cgc acc tgt gca gcc ttc tgc agg tca ctc agc      244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc      292
Cys Arg Lys Glu Gln Gly Lys Phe Tyr Asp His Leu Leu Arg Asp Cys
             80                  85                  90 atc agc tgt gcc tcc atc tgt gga cag cac cct aag caa tgt gca tac      340
Ile Ser Cys Ala Ser Ile Cys Gly Gln His Pro Lys Gln Cys Ala Tyr
         95                 100                 105 ttc tgt gag aac aag ctc agg agc gag ccc aaa tct tca gac aaa act      388
Phe Cys Glu Asn Lys Leu Arg Ser Glu Pro Lys Ser Ser Asp Lys Thr
110                 115                 120 cac aca tgc cca ccg tgc cca gca cct gaa gcc gag ggg gca ccg tca      436
His Thr Cys Pro Pro Cys Pro Ala Pro Glu Ala Glu Gly Ala Pro Ser
125                 130                 135                 140 gtc ttc ctc ttc ccc cca aaa ccc aag gac acc ctc atg atc tcc cgg      484
Val Phe Leu Phe Pro Pro Lys Pro Lys Asp Thr Leu Met Ile Ser Arg
                145                 150                 155 acc cct gag gtc aca tgc gtg gtg gtg gac gtg agc cac gaa gac cct      532
Thr Pro Glu Val Thr Cys Val Val Val Asp Val Ser His Glu Asp Pro
            160                 165                 170 gag gtc aag ttc aac tgg tac gtg gac ggc gtg gag gtg cat aat gcc      580
Glu Val Lys Phe Asn Trp Tyr Val Asp Gly Val Glu Val His Asn Ala
        175                 180                 185 aag aca aag ccg cgg gag gag cag tac aac agc acg tac cgt gtg gtc      628
Lys Thr Lys Pro Arg Glu Glu Gln Tyr Asn Ser Thr Tyr Arg Val Val
    190                 195                 200 agc gtc ctc acc gtc ctg cac cag gac tgg ctg aat ggc aag gag tac      676
Ser Val Leu Thr Val Leu His Gln Asp Trp Leu Asn Gly Lys Glu Tyr
205                 210                 215                 220 aag tgc aag gtc tcc aac aaa gcc ctc cca tcc tcc atc gag aaa acc      724
Lys Cys Lys Val Ser Asn Lys Ala Leu Pro Ser Ser Ile Glu Lys Thr
                225                 230                 235 atc tcc aaa gcc aaa ggg cag ccc cga gaa cca cag gtg tac acc ctg      772
Ile Ser Lys Ala Lys Gly Gln Pro Arg Glu Pro Gln Val Tyr Thr Leu
            240                 245                 250 ccc cca tcc cgg gat gag ctg acc aag aac cag gtc agc ctg acc tgc      820
Pro Pro Ser Arg Asp Glu Leu Thr Lys Asn Gln Val Ser Leu Thr Cys
        255                 260                 265 ctg gtc aaa ggc ttc tat ccc agc gac atc gcc gtg gag tgg gag agc      868
Leu Val Lys Gly Phe Tyr Pro Ser Asp Ile Ala Val Glu Trp Glu Ser
    270                 275                 280 aat ggg cag ccg gag aac aac tac aag acc acg cct ccc gtg ctg gac      916
Asn Gly Gln Pro Glu Asn Asn Tyr Lys Thr Thr Pro Pro Val Leu Asp
285                 290                 295                 300 tcc gac ggc tcc ttc ttc ctc tac agc aag ctc acc gtg gac aag agc      964
Ser Asp Gly Ser Phe Phe Leu Tyr Ser Lys Leu Thr Val Asp Lys Ser
                305                 310                 315 agg tgg cag cag ggg aac gtc ttc tca tgc tcc gtg atg cat gag gct     1012
Arg Trp Gln Gln Gly Asn Val Phe Ser Cys Ser Val Met His Glu Ala
            320                 325                 330 ctg cac aac cac tac acg cag aag agc ctc tcc ctg tct ccg ggt aaa     1060
Leu His Asn His Tyr Thr Gln Lys Ser Leu Ser Leu Ser Pro Gly Lys
        335                 340                 345
```
taatctagag gcgcgccaat ta                                                                        1082

<210> SEQ ID NO 21
<211> LENGTH: 348
<212> TYPE: PRT
<213> ORGANISM: Artificial Sequence
<220> FEATURE:
<223> OTHER INFORMATION: TACI-Fc fusion protein

<400> SEQUENCE: 21

```
Met Asp Ala Met Lys Arg Gly Leu Cys Cys Val Leu Leu Leu Cys Gly
  1               5                  10                  15

Ala Val Phe Val Ser Leu Ser Gln Glu Ile His Ala Glu Leu Arg Arg
             20                  25                  30

Phe Arg Arg Ala Met Arg Ser Cys Pro Glu Glu Gln Tyr Trp Asp Pro
         35                  40                  45

Leu Leu Gly Thr Cys Met Ser Cys Lys Thr Ile Cys Asn His Gln Ser
     50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
                 85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 22
<211> LENGTH: 1109
<212> TYPE: DNA
<213> ORGANISM: Artificial Sequence
<220> FEATURE:
<223> OTHER INFORMATION: TACI-Fc fusion protein
<220> FEATURE:
<221> NAME/KEY: CDS
<222> LOCATION: (17)...(1090)

<400> SEQUENCE: 22

```
tattaggccg gccacc atg gat gca atg aag aga ggg ctc tgc tgt gtg ctg         52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc          100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag          148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc          196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc          244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc          292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac          340
Ile Ser Cys Ala Ser Ile Cys Gly Gln His Pro Lys Gln Cys Ala Tyr
     95                 100                 105 ttc tgt gag aac aag ctc agg agc cca gtg aac ctt cca cca gag ctc          388
Phe Cys Glu Asn Lys Leu Arg Ser Pro Val Asn Leu Pro Pro Glu Leu
110                 115                 120 agg gag ccc aaa tct tca gac aaa act cac aca tgc cca ccg tgc cca          436
Arg Glu Pro Lys Ser Ser Asp Lys Thr His Thr Cys Pro Pro Cys Pro
125                 130                 135                 140 gca cct gaa gcc gag ggg gca ccg tca gtc ttc ctc ttc ccc cca aaa          484
Ala Pro Glu Ala Glu Gly Ala Pro Ser Val Phe Leu Phe Pro Pro Lys
                145                 150                 155 ccc aag gac acc ctc atg atc tcc cgg acc cct gag gtc aca tgc gtg          532
Pro Lys Asp Thr Leu Met Ile Ser Arg Thr Pro Glu Val Thr Cys Val
            160                 165                 170 gtg gtg gac gtg agc cac gaa gac cct gag gtc aag ttc aac tgg tac          580
Val Val Asp Val Ser His Glu Asp Pro Glu Val Lys Phe Asn Trp Tyr
        175                 180                 185 gtg gac ggc gtg gag gtg cat aat gcc aag aca aag ccg cgg gag gag          628
Val Asp Gly Val Glu Val His Asn Ala Lys Thr Lys Pro Arg Glu Glu
    190                 195                 200 cag tac aac agc acg tac cgt gtg gtc agc gtc ctc acc gtc ctg cac          676
Gln Tyr Asn Ser Thr Tyr Arg Val Val Ser Val Leu Thr Val Leu His
205                 210                 215                 220 cag gac tgg ctg aat ggc aag gag tac aag tgc aag gtc tcc aac aaa          724
Gln Asp Trp Leu Asn Gly Lys Glu Tyr Lys Cys Lys Val Ser Asn Lys
                225                 230                 235 gcc ctc cca tcc tcc atc gag aaa acc atc tcc aaa gcc aaa ggg cag          772
Ala Leu Pro Ser Ser Ile Glu Lys Thr Ile Ser Lys Ala Lys Gly Gln
            240                 245                 250 ccc cga gaa cca cag gtg tac acc ctg ccc cca tcc cgg gat gag ctg          820
Pro Arg Glu Pro Gln Val Tyr Thr Leu Pro Pro Ser Arg Asp Glu Leu
```

-continued

```
                 255                 260                 265
acc aag aac cag gtc agc ctg acc tgc ctg gtc aaa ggc ttc tat ccc     868
Thr Lys Asn Gln Val Ser Leu Thr Cys Leu Val Lys Gly Phe Tyr Pro
    270                 275                 280 agc gac atc gcc gtg gag tgg gag agc aat ggg cag ccg gag aac aac     916
Ser Asp Ile Ala Val Glu Trp Glu Ser Asn Gly Gln Pro Glu Asn Asn
285                 290                 295                 300 tac aag acc acg cct ccc gtg ctg gac tcc gac ggc tcc ttc ttc ctc     964
Tyr Lys Thr Thr Pro Pro Val Leu Asp Ser Asp Gly Ser Phe Phe Leu
            305                 310                 315 tac agc aag ctc acc gtg gac aag agc agg tgg cag cag ggg aac gtc    1012
Tyr Ser Lys Leu Thr Val Asp Lys Ser Arg Trp Gln Gln Gly Asn Val
        320                 325                 330 ttc tca tgc tcc gtg atg cat gag gct ctg cac aac cac tac acg cag    1060
Phe Ser Cys Ser Val Met His Glu Ala Leu His Asn His Tyr Thr Gln
    335                 340                 345 aag agc ctc tcc ctg tct ccg ggt aaa taa tctagaggcg cgccaatta       1109
Lys Ser Leu Ser Leu Ser Pro Gly Lys *
    350                 355
```

<210> SEQ ID NO 23
<211> LENGTH: 357
<212> TYPE: PRT
<213> ORGANISM: Artificial Sequence
<220> FEATURE:
<223> OTHER INFORMATION: TACI-Fc fusion protein

<400> SEQUENCE: 23

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Glu Pro Lys
        115                 120                 125

Ser Ser Asp Lys Thr His Thr Cys Pro Pro Cys Pro Ala Pro Glu Ala
    130                 135                 140

Glu Gly Ala Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ser
```

```
                225                 230                 235                 240
Ser Ile Glu Lys Thr Ile Ser Lys Ala Lys Gly Gln Pro Arg Glu Pro
                    245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
        290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 24
<211> LENGTH: 311
<212> TYPE: PRT
<213> ORGANISM: Artificial Sequence
<220> FEATURE:
<223> OTHER INFORMATION: BAFF-R-Fc fusion protein

<400> SEQUENCE: 24

Met Ser Ala Leu Leu Ile Leu Ala Leu Val Gly Ala Ala Val Ala Ser
1               5                   10                  15

Thr Arg Arg Gly Pro Arg Ser Leu Arg Gly Arg Asp Ala Pro Ala Pro
                20                  25                  30

Thr Pro Cys Val Pro Ala Glu Cys Phe Asp Leu Leu Val Arg His Cys
            35                  40                  45

Val Ala Cys Gly Leu Leu Arg Thr Pro Arg Pro Lys Pro Ala Gly Ala
        50                  55                  60

Ser Ser Pro Ala Pro Arg Thr Ala Leu Gln Pro Gln Glu Ser Gln Val
65                  70                  75                  80

Thr Asp Lys Ala Ala His Tyr Thr Leu Cys Pro Pro Cys Pro Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Ala Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Glu Glu Met Thr Lys
    210                 215                 220

Asn Gln Val Ser Leu Thr Cys Leu Val Lys Gly Phe Tyr Pro Ser Asp
```

```
                    225                 230                 235                 240
Ile Ala Val Glu Trp Glu Ser Asn Gly Gln Pro Glu Asn Asn Tyr Lys
                        245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
                275                 280                 285

Cys Ser Val Met His Glu Ala Leu His Asn His Tyr Thr Gln Lys Ser
        290                 295                 300

Leu Ser Leu Ser Pro Gly Lys
305                 310

<210> SEQ ID NO 25
<211> LENGTH: 1348
<212> TYPE: DNA
<213> ORGANISM: homo sapiens
<220> FEATURE:
<221> NAME/KEY: CDS
<222> LOCATION: (282)...(1034)

<400> SEQUENCE: 25
ggtacgaggc ttcctagagg gactggaacc taattctcct gaggctgagg gagggtggag       60
ggtctcaagg caacgctggc cccacgacgg agtgccagga gcactaacag tacccttagc      120
ttgctttcct cctccctcct ttttattttc aagttccttt ttatttctcc ttgcgtaaca      180
accttcttcc cttctgcacc actgcccgta cccttacccg ccccgccacc tccttgctac      240
cccactcttg aaaccacagc tgttggcagg gtccccagct c atg cca gcc tca tct      296
                                             Met Pro Ala Ser Ser
                                              1               5 cct ttc ttg cta gcc ccc aaa ggg cct cca ggc aac atg ggg ggc cca      344
Pro Phe Leu Leu Ala Pro Lys Gly Pro Pro Gly Asn Met Gly Gly Pro
             10                  15                  20 gtc aga gag ccg gca ctc tca gtt gcc ctc tgg ttg agt tgg ggg gca      392
Val Arg Glu Pro Ala Leu Ser Val Ala Leu Trp Leu Ser Trp Gly Ala
         25                  30                  35 gct ctg ggg gcc gtg gct tgt gcc atg gct ctg ctg acc caa caa aca      440
Ala Leu Gly Ala Val Ala Cys Ala Met Ala Leu Leu Thr Gln Gln Thr
     40                  45                  50 gag ctg cag agc ctc agg aga gag gtg agc cgg ctg cag ggg aca gga      488
Glu Leu Gln Ser Leu Arg Arg Glu Val Ser Arg Leu Gln Gly Thr Gly
 55                  60                  65 ggc ccc tcc cag aat ggg gaa ggg tat ccc tgg cag agt ctc ccg gag      536
Gly Pro Ser Gln Asn Gly Glu Gly Tyr Pro Trp Gln Ser Leu Pro Glu
 70                  75                  80                  85 cag agt tcc gat gcc ctg gaa gcc tgg gag aat ggg gag aga tcc cgg      584
Gln Ser Ser Asp Ala Leu Glu Ala Trp Glu Asn Gly Glu Arg Ser Arg
                 90                  95                 100 aaa agg aga gca gtg ctc acc caa aaa cag aag aag cag cac tct gtc      632
Lys Arg Arg Ala Val Leu Thr Gln Lys Gln Lys Lys Gln His Ser Val
            105                 110                 115 ctg cac ctg gtt ccc att aac gcc acc tcc aag gat gac tcc gat gtg      680
Leu His Leu Val Pro Ile Asn Ala Thr Ser Lys Asp Asp Ser Asp Val
        120                 125                 130 aca gag gtg atg tgg caa cca gct ctt agg cgt ggg aga ggc cta cag      728
Thr Glu Val Met Trp Gln Pro Ala Leu Arg Arg Gly Arg Gly Leu Gln
    135                 140                 145 gcc caa gga tat ggt gtc cga atc cag gat gct gga gtt tat ctg ctg      776
Ala Gln Gly Tyr Gly Val Arg Ile Gln Asp Ala Gly Val Tyr Leu Leu
150                 155                 160                 165
```

```
tat agc cag gtc ctg ttt caa gac gtg act ttc acc atg ggt cag gtg    824
Tyr Ser Gln Val Leu Phe Gln Asp Val Thr Phe Thr Met Gly Gln Val
                170                 175                 180 gtg tct cga gaa ggc caa gga agg cag gag act cta ttc cga tgt ata    872
Val Ser Arg Glu Gly Gln Gly Arg Gln Glu Thr Leu Phe Arg Cys Ile
            185                 190                 195 aga agt atg ccc tcc cac ccg gac cgg gcc tac aac agc tgc tat agc    920
Arg Ser Met Pro Ser His Pro Asp Arg Ala Tyr Asn Ser Cys Tyr Ser
        200                 205                 210 gca ggt gtc ttc cat tta cac caa ggg gat att ctg agt gtc ata att    968
Ala Gly Val Phe His Leu His Gln Gly Asp Ile Leu Ser Val Ile Ile
    215                 220                 225 ccc cgg gca agg gcg aaa ctt aac ctc tct cca cat gga acc ttc ctg   1016
Pro Arg Ala Arg Ala Lys Leu Asn Leu Ser Pro His Gly Thr Phe Leu
230                 235                 240                 245 ggg ttt gtg aaa ctg tga ttgtgttata aaaagtggct cccagcttgg          1064
Gly Phe Val Lys Leu *
                250 aagaccaggg tgggtacata ctggagacag ccaagagctg agtatataaa ggagagggaa 1124 tgtgcaggaa cagaggcatc ttcctgggtt tggctccccg ttcctcactt ttcccttttc 1184 attcccaccc cctagacttt gattttacgg atatcttgct tctgttcccc atggagctcc 1244 gaattcttgc gtgtgtgtag atgaggggcg gggacgggc gccaggcatt gttcagacct  1304 ggtcggggcc cactggaagc atccagaaca gcaccaccat ctta                  1348

<210> SEQ ID NO 26
<211> LENGTH: 250
<212> TYPE: PRT
<213> ORGANISM: homo sapiens

<400> SEQUENCE: 26

Met Pro Ala Ser Ser Pro Phe Leu Leu Ala Pro Lys Gly Pro Pro Gly
 1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190
```

```
Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
            245                 250
```

LEVELS OF BLYS/APRIL HETEROTRIMERS IN SERUM AND USE IN DIAGNOSTIC METHODS

CROSS-REFERENCE TO RELATED APPLICATIONS

This application is a divisional of U.S. application Ser. No. 12/428,146, filed Apr. 22, 2009, which claims the benefit of U.S. Provisional Application No. 61/049,706, filed May 1, 2008, both of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 436925seqlist-.txt, a creation date of Aug. 21, 2013, and a size of 66 KB. The sequence listing filed via EFS-Web is part of the specification and is hereby incorporated in its entirety by reference herein.

BACKGROUND OF THE INVENTION

Cellular interactions which occur during an immune response are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (Smith et al., *The TNF Receptor Superfamily of Cellular and Viral Proteins: Activation, Costimulation and Death*, 76:959-62, 1994; Cosman, *Stem Cells* 12:440-55, 1994). Three receptor members of this family are (1) BCMA, B Cell Maturation Antigen (Gras et al., *Int. Immunol.* 17:1093-106, 1995 and Hatzoglou et al., *J. Immunol.*, 165: 1322-30, 2000); (2) TACI, transmembrane activator and CAML-interactor (von Bülow and Bram, *Science* 228:138-41, 1997 and WIPO Publication WO 98/39361)) and (3) BAFF-R, also known as BLyS/BLyS receptor 3 (BR3), (Thompson et al., *Science,* 293: 2108-11, 2001). These receptors are known to bind one or both TNF ligands—B Lymphocyte stimulator (BLyS also known as BLyS, TALL-1, ztnf4 and THANK) (see, e.g., Shu et al., *J. Leukoc. Biol.* 65: 680-683 (1999)) and a proliferation-inducing ligand (APRIL) (see, e.g., Hahne et al., *J. Exp. Med.* 188: 1185-1190 (1998)). Specifically, TACI and BCMA are known to bind both BLyS and APRIL and BAFF-R binds only BLyS.

A number of BLyS and/or APRIL antagonists have been developed in order to block the binding of the ligands to the receptor members of the family, in order to block results of this binding which include but should not be limited to B cell co-stimulation, plasmablast and plasma cell survival, Ig class switching, enhanced B-cell antigen presenting cell function, survival of malignant B cells, development of B-1 cell function, B cell development beyond the T-1 stage, and complete germinal centre formation. Some of these molecules can also bind to and block the effect of APRIL on B cells and other components of the immune system (Dillon et al. (2006) Nat. Rev. Drug Dis. 5, 235-246). Molecules that have been developed to affect B cell function by interfering with BLyS and/or APRIL binding include BLyS antibodies such as Lymphostat-B (Belimumab) (Baker et al, (2003) Arthritis Rheum, 48, 3253-3265 and WO 02/02641); receptor-extracellular domain/Fc domain fusions proteins such as TACI-Ig, including one particular embodiment, atacicept (U.S. Patent Application No. 20060034852), BAFF-R-Fc (WO 05/0000351), and BCMA-Ig or other fusion proteins utilizing receptor extracellular domains. A further class of BLyS and/or APRIL antagonists include other molecules relying on BLyS binding ability to block binding to its receptors such as AMG 623, receptor antibodies, and other molecules disclosed in WO 03/035846 and WO 02/16312.

One understudied aspect of this ligand/receptor family is the fact that these ligands appear to exist in vivo not only as homotrimers (which would be expected for TNF family ligands), but also as BLyS/APRIL heterotrimers (HT) of uncharacterized stoichiometry. Using an extremely small and heterogenous sample set (i.e., 15 patients with 6 different autoimmune disease diagnosies between them), the existence of elevated HT in sera as compared to healthy controls was reported by Roschke et al. (J. Immunol. 169:4314-4321, 2002). However, there has been no association of the presence of elevated HT with any particular autoimmune disease, an analysis necessary to apply such findings to specific disease treatment methods nor has this finding been presented beyond anecdotally, i.e., with statistical significance.

Thus, there remains a need in the art for investigation into the biological activity of HT and the development of an assay to compare the levels of native HT to those of homotrimeric BLyS and APRIL in autoimmune patients. Furthermore, this assay allows identification of expression patterns of HT so that statistical associations with autoimmune disease can be identified, such as systemic lupus erythematosus (SLE). Such information is important for identifying individuals who have a propensity toward developing such autoimmune diseases, are in an active disease state, and for identifying those that will respond favorably to BLyS and/or APRIL antagonist treatment of these diseases. The present invention addresses this need by providing HT levels associated with autoimmune diseases and providing diagnostic tests determining the presence of this expression pattern, namely increased HT levels in serum for those suffering from autoimmune disease such as SLE as compared to levels seen in healthy controls.

SUMMARY OF THE INVENTION

The present invention provides a method of screening for levels of HT in serum and in other biological samples. As it has been shown that elevated levels of HT are significantly associated with autoimmune disease, such as RA, this measurement is useful as a diagnostic assay. Such diagnostic assays are useful in predicting an individual's likelihood of having a condition associated with autoimmune activity, such as SLE. The invention further provides methods for determining an appropriate treatment for an individual with an autoimmune disease, such as SLE.

Detection of high levels of HT in the serum of patients exhibiting autoimmune activity, such as SLE, allows selection of a treatment plan that is most likely to be effective in treating the condition. These treatment plans generally involve the use of BLyS and/or APRIL antagonists, either singly or in combination with another pharmaceutical such as an immune suppressive drug (like MMF or Cellcept®) or a CD 20 antagonist (like Rituxan®).

Thus, the invention further provides methods for treating an individual newly clinically diagnosed with an autoimmune condition, generally comprising detecting high levels of HT in the serum, as compared to levels seen in the serum of healthy controls, and selecting a treatment plan that is most effective for individuals clinically diagnosed with an autoimmune disease. Detection of high levels of HT in the serum also allows one to predict a patient's likelihood to respond to a specific drug treatment, particularly BLyS and/or APRIL antagonists. Thus, the invention further provides methods of predicting a patient's likelihood to respond to BLyS and/or APRIL antagonists (either singly or in combination with other drugs) during treatment for an autoimmune condition, such as SLE.

Very specifically, the present invention describes a method of detecting increased HT levels in the serum of an individual comprising measuring a first level of HT protein levels in a biological sample and comparing that level to a second level of HT protein levels present in a biological sample of a healthy individual and determining the first level is increased as compared to the second level, wherein said increased HT protein levels is associated with an autoimmune disease. The autoimmune disease in the present invention can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

The present invention also describes a method of treating an individual clinically diagnosed with an autoimmune disease, comprising analyzing a biological sample from an individual clinically diagnosed with autoimmune disease for the presence or absence of elevated HT levels in serum, wherein the presence of elevated HT levels is associated with the clinical diagnosis of autoimmune disease; and selecting a treatment plan that is most effective for individuals clinically diagnosed as having a condition associated with an increased HT levels. The treatment plan can involve administration of a BLyS antagonist. And, in a preferred embodiment said BLyS antagonist can also be an APRIL antagonist. In particular, the treatment plan should involve the administration of a HT antagonist. For this method the autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

Furthermore, the present invention describes methods for predicting a patient's likelihood to respond to a drug treatment for an autoimmune disease, comprising determining the level of HT levels in the serum, wherein the presence of elevated HT levels is predictive of the patient's likelihood to respond to a drug treatment for the condition. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura ('TTP), autoimmune thrombocytopenia, multiple sclerosis, psoriasis, IgA nephropathy, IgM polyneuropathies, myasthenia gravis, diabetes mellitus, Reynaud's syndrome, Sjorgen's syndrome and glomerulonephritis. In particular, the autoimmune disease is SLE. Additionally, the present invention method can include a drug treatment involves administration of a HT antagonist, which can also be a BLyS and/or APRIL antagonist.

The present invention also encompasses an in vitro method of detecting increased HT levels in the serum of an individual, comprising measuring the level of HT levels in a test biological sample from the individual; comparing that level to the level of HT levels in a biological sample from a healthy control; and determining whether the level of HT levels in the test biological sample is increased as compared to the level in the control sample; wherein said increased HT levels is associated with an autoimmune disease. The autoimmune disease in this method can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

In a further embodiment, the present invention includes an in vitro method of selecting a treatment plan that is most effective for treating an individual clinically diagnosed with an autoimmune disease, comprising analyzing in vitro a biological sample from an individual clinically diagnosed with autoimmune disease for the presence or absence of elevated HT levels in their serum, wherein the presence of elevated HT levels is associated with the clinical diagnosis of autoimmune disease. For this method, the treatment plan can involves the use of a HT antagonist and the HT antagonist can also be a BLyS and/or APRIL antagonist. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE.

In a still further embodiment, the present invention includes an in vitro method for predicting a patient's likelihood to respond to a drug treatment for an autoimmune disease, comprising determining the level of HT levels in a sample from the patient; wherein the presence of elevated HT levels is predictive of the patient's likelihood to respond to a drug treatment for the condition. The autoimmune disease can be selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. In particular, the autoimmune disease is SLE. The drug treatment of the present invention can comprise a HT antagonist and said HT antagonist can also be a BLyS and/or APRIL antagonist.

Finally, the present invention contemplates a BLys antagonist for use in the treatment of an autoimmune disease in a patient, wherein said patient has elevated levels of HT levels in the serum. The antagonist can also be a receptor-extracellular domain/Fc domain fusion protein selected from TACI-Ig and BCMA-Ig. In particular, the receptor-extracellular domain/Fc domain fusion protein can be TACI-Ig, such as atacicept.

These and other aspects of the invention will become apparent to those persons skilled the art upon reading the details of the invention as more fully described below.

BRIEF DESCRIPTION OF THE INVENTION

Figure 1:
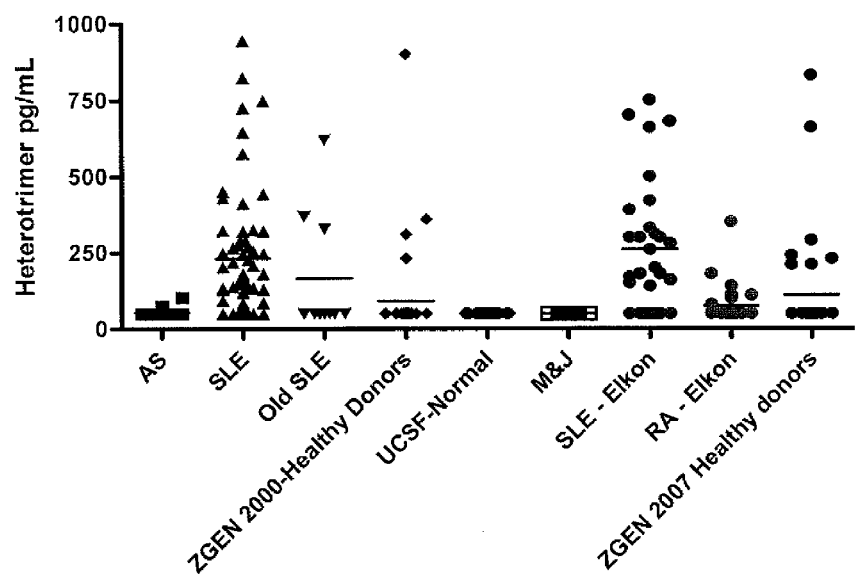
FIG. 1. is a scatter graph of the heterotrimer levels for a cohort of patients diagnosed with SLE or RA as well as healthy controls.

The present invention provides a method for screening HT levels in biological samples, such as serum and the use of this information for predicting the presence of autoimmune disease and predicting the likelihood that a patient would respond to HT antagonist treatment. The invention is based on the finding that the levels of HT levels in the serum of autoimmune patients is statistically elevated. HT antagonists (which may also be BLyS and/or APRIL antagonists) selectively neutralize the production of autoimmune immunoglobulin and other tissue destructive cytokines by the immune cells, such as B cells, of said patients. This observation allows development of diagnostic assays to detect the presence of increased HT levels where these higher levels are associated with autoimmune disease, such as SLE, and also may predict the likelihood that an individual will successfully respond to treatment methods that neutralize the action of reactive immune cells, such as B cells, i.e., HT antagonists (BLyS and/or APRIL antagonists).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term heterotrimer (HT), as used herein encompasses multimers of three ligand subunits, where each ligand subunit is either BLyS or APRIL and at least one subunit is BLyS and at least one subunit is APRIL. Thus, "HT" includes those molecules that are 2 BLyS and one APRIL, as well as those that are 2 APRIL and one BLyS.

The term "polymorphism", as used herein, refers to a difference in the nucleotide or amino acid sequence of a given region as compared to a nucleotide or amino acid sequence in a homologous-region of another individual, in particular, a difference in the nucleotide of amino acid sequence of a given region which differs between individuals of the same species. A polymorphism is generally defined in relation to a reference sequence. Polymorphisms include single nucleotide differences, differences in sequence of more than one nucleotide, and single or multiple nucleotide insertions, inversions and deletions; as well as single amino acid differences, differences in sequence of more than one amino acid, and single or multiple amino acid insertions, inversions, and deletions.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

In the broadest sense, as used herein, the terms "autoimmune disease," refer to a disease wherein a patient's immune system is producing an unwanted immune response to one or more of their own proteins. Representative examples of autoimmune diseases include rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as: where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

Stringent conditions for both DNA/DNA and DNA/RNA hybridization are as described by Sambrook et al. Molecular Cloning, A Laboratory Manual, 2nd Ed., Cold Spring Harbor Laboratory Press, Cold Spring Harbor, N.Y., 1989, herein incorporated by reference. For example, see page 7.52 of Sambrook et al.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vivo or in vitro with a recombinant vector or a polynucleotide of the invention. A host cell which comprises a recombinant vector of the invention is a "recombinant host cell".

The term "binds specifically," in the context of antibody binding, refers to high avidity and/or high affinity binding of an antibody to a specific polypeptide i.e., epitope of a polymorphic APRIL or BLyS polypeptide. Antibody binding to an epitope on a specific APRIL or BLyS polypeptide is preferably stronger than binding of the same antibody to any other epitope, particularly those which may be present in molecules in association with, or in the same sample, as the specific polypeptide of interest, e.g., binds more strongly to a specific APRIL or BLyS epitope than to a different APRIL or BLyS epitope so that by adjusting binding conditions the antibody binds almost exclusively to the specific APRIL or BLyS epitope and not to any other APRIL or BLyS epitope. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific APRIL or BLyS polypeptide with a binding affinity of $10^7$ mole/l or more, preferably $10^8$ mole/l or more are said to bind specifically to the specific APRIL or BLyS polypeptide. In general, an antibody with a binding affinity of $10^6$ mole/liters or less is not useful in that it will not bind an antigen at a detectable level using conventional methodology currently used.

The term "monoclonal antibody" as used herein refers to an antibody obtained from a population of substantially homogeneous antibodies, i.e., the individual antibodies comprising the population are identical except for possible naturally occurring mutations that can be present in minor amounts.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin.

For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992). The humanized antibody includes a PRIMATIZED antibody wherein the antigen-binding region of the antibody is derived from an antibody produced by, e.g., immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1): 86-95 (1991).

"Functional fragments" of the binding antibodies of the invention are those fragments that retain binding to BLyS, TALI, BAFF-R, or BCMA with substantially the same affinity as the intact full chain molecule from which they are derived and may be able to deplete B cells as measured by in vitro or in vivo assays such as those described herein.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing-target cell and subsequently kill the-target cell with cytotoxins. The antibodies-"arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Ann. Rev. Immunol 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95: 652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoroetal., J. Immunol. Methods 202: 163 (1996), may be performed.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

Isolated antibody includes the antibody in situ within recombinant cells since at least one component of the antibody's natural environment will not be present. Ordinarily, however, isolated antibody will be prepared by at least one purification step.

The terms "detectably labeled antibody" refers to an antibody (or antibody fragment which retains binding specificity for a APRIL polypeptide or epitope), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)).

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

"Immunosuppressive drugs" are any molecules that interfere with the immune system and blunt its response to foreign or self antigens. Cyclophosphamide (CYC) and mycophenolate mofetil (MMF) are two such kinds of molecules. This term is intended to encompass any drug or molecule useful as a therapeutic agent in downregulating the immune system.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

A "conjugate" refers to any hybrid molecule, including fusion proteins and as well as molecules that contain both amino acid or protein portions and non-protein portions. Conjugates may be synthesized by a variety of techniques known in the art including, for example, recombinant DNA techniques, solid phase synthesis, solution phase synthesis, organic chemical synthetic techniques or a combination of these techniques. The choice of synthesis will depend upon the particular molecule to be generated. For example, a hybrid molecule not entirely "protein" in nature may be synthesized by a combination of recombinant techniques and solution phase techniques.

As used herein, the term "Fc-fusion protein" designates antibody-like molecules which combine the binding specificity of a heterologous protein with the effector functions of immunoglobulin constant domains. Structurally, the Fc-fusion proteins comprise a fusion of an amino acid sequence with the desired binding specificity which is other than the antigen recognition and binding site of an antibody (i.e., is "heterologous"), and an immunoglobulin constant domain sequence. The Fc-fusion protein molecule typically includes a contiguous amino acid sequence comprising at least the binding site of a receptor or a ligand. The immunoglobulin constant domain sequence in the Fc-fusion protein can be obtained from any immunoglobulin, such as IgG-1, IgG-2, IgG-3, or IgG-4 subtypes, IgA (including IgA-1 and IgA-2), IgE, IgD or IgM. For example, useful Fc-fusion proteins according to this invention are polypeptides that comprise the BLyS binding portions of a BLyS receptor without the transmembrane or cytoplasmic sequences of the BLyS receptor. In one embodiment, the extracellular domain of BAFF-R, TACI or BCMA is fused to a constant domain of an immunoglobulin sequence.

The terms "individual," "subject," and "patient," used interchangeably herein, refer to a mammal, including, but not limited to, murines, simians, humans, mammalian farm animals, mammalian sport animals, and mammalian pets.

The term "mammal" refers to any animal classified as a mammal, including humans, domestic and farm animals, and zoo, sports, or pet animals, such as dogs, horses, cats, cows, etc. Preferably, the mammal herein is human.

Detection of HT (APRIL and BLyS Polypeptides)

The present invention provides for detection of HT polypeptides through the separate measurement of APRIL and BLyS polypeptides. The term "APRIL polypeptide" encompasses an amino acid sequence encoded by an open reading frame (ORF) of a known APRIL polynucleotide (such as those publicly available, GenBank Accession number AF046888), including the full-length native polypeptide and fragments thereof, particularly biologically active fragments and/or fragments corresponding to functional domains, e.g. a region or domain having biological activity, etc.; antigenic fragments thereof, and including fusions of the subject polypeptides to other proteins or parts thereof. The amino acid sequences of APRIL polypeptides have been disclosed. (See e.g. Hahne et al., *J. Exp. Med.* 188: 1185-90, 1998). The APRIL polypeptides of the invention can be isolated from a variety of sources, such as from human tissue types or from another source, or prepared by recombinant and/or synthetic methods. A polymorphism in an APRIL polypeptide is generally defined relative to a reference sequence.

The term "BLyS polypeptide" encompasses an amino acid sequence encoded by an open reading frame (ORF) of a known BLyS polynucleotide (such as those publicly available through GenBank or its complement: Accession No. NM 052945 (human BLyS mRNA) or its human variants Accession Nos. 003808, 172087, 172088 or Accession No. 033622 (mouse BLyS mRNA)), including the full-length native polypeptide and fragments thereof, particularly biologically active fragments and/or fragments corresponding to functional domains, e.g. a region or domain having biological activity, etc.; antigenic fragments thereof, and including fusions of the subject polypeptides to other proteins or parts thereof. The amino acid sequences of BLyS polypeptides have been disclosed. (See e.g. Moore et al. Science 285: 260-3, 1999). The BLyS polypeptides of the invention can be isolated from a variety of sources, such as from human tissue types or from another source, or prepared by recombinant and/or synthetic methods. A polymorphism in a BLyS polypeptide is generally defined relative to a reference sequence.

As used herein, "polymorphic APRIL polypeptide" refers to an amino acid sequence of a recombinant or non-recombinant polypeptide having an amino acid sequence of i) a native polymorphic APRIL polypeptide, ii) a fragment of a polymorphic APRIL polypeptide, iii) polypeptide analogs of a polymorphic APRIL polypeptide, iv) variants of a polymorphic APRIL polypeptide; v) an immunologically active fragment of a polymorphic APRIL polypeptide; and vi) fusion proteins comprising a polymorphic APRIL polypeptide. Polymorphic APRIL polypeptides of the invention can be obtained from a biological sample, or from any source whether natural, synthetic, semi-synthetic or recombinant.

As used herein, "polymorphic BLyS polypeptide" refers to an amino acid sequence of a recombinant or non-recombinant polypeptide having an amino acid sequence of i) a native polymorphic BLyS polypeptide, ii) a fragment of a polymorphic BLyS polypeptide, iii) polypeptide analogs of a polymorphic BLyS polypeptide, iv) variants of a polymorphic BLyS polypeptide; v) an immunologically active fragment of a polymorphic BLyS polypeptide; and vi) fusion proteins comprising a polymorphic BLyS polypeptide. Polymorphic BLyS polypeptides of the invention can be obtained from a biological sample, or from any source whether natural, synthetic, semi-synthetic or recombinant.

The term "BLyS polypeptide" or "APRIL polypeptide" encompasses a polypeptide comprising from at least about 5 amino acids, at least about 10 amino acids, at least about 15 amino acids, at least about 25 amino acids, at least about 50 amino acids, at least about 75 amino acids, at least about 100 amino acids, at least about 200 amino acids, at least about 300 amino acids, at least about 400 amino acids, or up to the entire polypeptide of a polymorphic APRIL or BLyS polypeptide. In some embodiments, a polymorphic APRIL or BLyS polypeptide exhibits biological activity, e.g., the polypeptide causes proliferation of B-cells and production of immunoglobulin in an in vitro assay. Other assays for APRIL or BLyS biological activity are known in the art and can be used to determine whether a polymorphic APRIL or BLyS polypeptide exhibits biological activity and, if desired, to quantitate APRIL or BLyS biological activity. APRIL or BLyS biological assays are described in various publications, e.g. Moore et al., supra.

APRIL polypeptides can be obtained by any known method, or a combination of such methods, including isolation from natural sources; production by chemical synthesis; and production by standard recombinant techniques. APRIL polypeptides can be isolated from a biological source, using affinity chromatography, e.g., using antibodies specific for a APRIL polypeptide are immobilized on a solid support. The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, CHO cells, HEK293 cells, and the like, may be used as the expression host cells. In some situations, it is desirable to express the gene in eukaryotic cells, where the protein will benefit from native folding and post-translational modifications. The polypeptide can then be isolated from cell culture supernatant or from cell lysates using affinity chromatography methods or anion exchange/size exclusion chromatography methods, as described above.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The isolated proteins can be used to produce antibodies, which are in turn, used to detect the presence of that protein using standard assay systems, e.g., ELISA or FACS analysis.

Preparation of APRIL and BLyS Polypeptides

In addition to the plurality of uses described in greater detail in following sections, the APRIL nucleic acid compositions are used in the preparation of all or a portion of the APRIL polypeptides, as described above. The polynucleotides (including cDNA or the full-length gene) are used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., Gene (Amsterdam) (1995) 164(1):49-53. In this method, assembly PCR (the synthesis of long DNA sequences from large numbers of oligodeoxyribonucleotides (oligos)) is described. The method is derived from DNA shuffling (Stemmer, Nature (1994) 370:389-391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., Molecular Cloning: A Laboratory Manual, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

In particular it may be necessary to provide engineered means of trimerizing the APRIL protein or the BLyS protein in order to be able to produce sufficient amounts of active protein to produce effective antibodies. Examples of trimerizing polypeptides such as the ZymoZipper sequence are disclosed in U.S. patent application Ser. No. 11/530,672 and the references discussed therein. These types of trimerizing polypeptides are also useful for producing APRIL/BLyS HT standard protein for use in the assay (see Example 1).

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a APRIL polypeptide-encoding polynucleotide is linked to a regulatory sequence as appropriate to obtain the desired expression properties. These-can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the APRIL gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

APRIL polypeptides may be expressed in prokaryotes or eukaryotes in accordance with conventional ways, depending upon the purpose for expression. For large scale production of the protein, a unicellular organism, such as $E.$ $coli,$ $B.$ $subtilis,$ $S.$ $cerevisiae,$ insect cells in combination with baculovirus vectors, or cells of a higher organism such as vertebrates, particularly mammals, e.g. COS 7 cells, HEK 293, CHO, *Xenopus Oocytes*, etc., may be used as the expression host cells. In some situations, it is desirable to express a polymorphic APRIL nucleic acid molecule in eukaryotic cells, where the polymorphic APRIL protein will benefit from native folding and post-translational modifications. Small peptides can also be synthesized in the laboratory. Polypeptides that are subsets of the complete APRIL sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., Nature (1978) 275:615; Goeddel et al., Nature (1979) 281:544; Goeddel et al., Nucleic Acids Res. (1980) 8:4057; EP 0 036,776; U.S. Pat. No. 4,551,433; DeBoer et al., Proc. Natl. Acad. Sci. (USA) (1983) 80:21-25; and Siebenlist et al., Cell (1980) 20:269.

Yeast. Expression systems in yeast include those described in Hinnen et al., Proc. Natl. Acad. Sci. (USA) (1978) 75:1929; Ito et al., J. Bacteriol. (1983) 153:163; Kurtz et al., Mol. Cell. Biol. (1986) 6:142; Kunze et al., J. Basic Microbiol. (1985) 25:141; Gleeson et al., J. Gen. Microbiol. (1986) 132:3459; Roggenkamp et al., Mol. Gen. Genet. (1986) 202:302; Das et al., J. Bacteriol. (1984) 158:1165; De Louvencourt et al., J. Bacteriol. (1983) 154:737; Van den Berg et al., Bio/Technology (1990)8:135; Kunze et al., J. Basic Microbiol. (1985)25: 141; Cregg et al., Mol. Cell. Biol. (1985) 5:3376; U.S. Pat. Nos. 4,837,148 and 4,929,555; Beach and Nurse, Nature (1981) 300:706; Davidow et al., Curr. Genet. (1985) 10:380; Gaillardin et al., Curr. Genet. (1985) 10:49; Ballance et al., Biochem. Biophys. Res. Commun. (1983) 112:284-289; Tilburn et al., Gene (1983) 26:205-221; Yelton et al., Proc. Natl. Acad. Sci. (USA) (1984) 81:1470-1474; Kelly and Hynes, EMBO J. (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: The Molecular Biology Of Baculoviruses (1986) (W. Doerfler, ed.); EP 0 127,839; EP 0 155,476; and Vlak et al., J. Gen. Virol. (1988) 69:765-776; Miller et al., Ann. Rev. Microbiol. (1988) 42:177; Carbonell et al., Gene (1988) 73:409; Maeda et al., Nature (1985) 315:592-594; Lebacq-Verheyden et al., Mol. Cell. Biol. (1988) 8:3129; Smith et al., Proc. Natl. Acad. Sci. (USA) (1985) 82:8844; Miyajima et al., Gene (1987) 58:273; and Martin et al., DNA (1988) 7:99. Numerous baculoviral strains and variants and corresponding permissive insect host cells from hosts are described in Luckow et al., Bio/Technology (1988) 6:47-55, Miller et al., Generic Engineering (1986) 8:277-279, and Maeda et al., Nature (1985) 315:592-594.

Mammalian Cells. Mammalian expression is accomplished as described in Dijkema et al., EMBO J. (1985) 4:761, Gorman et al., Proc. Natl. Acad. Sci. (USA) (1982) 79:6777, Boshart et al., Cell (1985) 41:521 and U.S. Pat. No. 4,399, 216. Other features of mammalian expression are facilitated as described in Ham and Wallace, Meth. Enz. (1979) 58:44, Barnes and Sato, Anal. Biochem. (1980) 102:255, U.S. Pat. Nos. 4,767,704, 4,657,866, 4,927,762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of APRIL proteins without manipulation of the encoding nucleic acid itself, but instead through integration of a regulatory sequence into the genome of cell that already includes a gene encoding the desired protein, as described in the above incorporated patent documents.

Preparation of Antibodies Specific for APRIL and BLyS Polypeptides

The invention further can encompass the use of antibodies, particularly isolated antibodies, that are specific for APRIL and BLyS polypeptides. The antibodies of the invention are useful in a variety of diagnostic assays, as described in further detail below. For example, the antibodies can be used to detect and/or measure the levels of HT in a biological sample.

Isolated APRIL and BLyS polypeptides of the invention are useful for the production of antibodies, where short fragments provide for antibodies specific for the particular polypeptide, and larger fragments or the entire protein allow for the production of antibodies over the surface of the polypeptide. Accordingly, the methods of the present invention can utilize isolated antibodies which specifically bind a APRIL polypeptide, or antigenic fragment thereof. Antibodies may be raised to the wild-type or variant forms. Antibodies may be raised to isolated peptides corresponding to these domains, or to the native protein. Antibodies may be raised to polypeptides and/or peptide fragments of APRIL from any mammalian species. As one non-limiting example, an enzyme-linked immunosorbent assay (ELISA) can be used to determine the specificity of a given monoclonal antibody for a APRIL or BLyS polypeptide.

The APRIL and BLyS polypeptides are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, fusion proteins comprising such antibody fragments, detectably labeled antibodies, and chimeric antibodies. "Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies for an APRIL or BLyS polypeptide.

Antibodies are prepared in accordance with conventional ways, where the expressed is polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage display libraries, usually in conjunction with in vitro affinity maturation.

Antibodies may be attached, directly or indirectly (e.g., via a linker molecule) to a solid support for use in a diagnostic assay to determine and/or measure the presence of HT in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies attached to a solid support.

A single antibody or a battery of different antibodies can then be used to create an assay device. Such an assay device can be prepared using conventional technology known to those skilled in the art. The antibody can be purified and isolated using known techniques and bound to a support surface using known procedures. The resulting surface having antibody bound thereon can be used to assay a test sample, e.g., a biological sample, in vitro to determine if the sample contains one or more types of HT molecules. For example, antibodies which bind only to a specific HT epitope can be attached to the surface of a material. Alternatively, a plurality of specific antibodies, which may be arranged in an array, wherein antibodies specific for two or more different HT epitopes are attached to the solid support, can be used. A test sample is brought into contact with the antibodies bound to the surface of material. Specific binding can be detected using any known method. If specific binding is not detected, it can be deduced that the sample does not contain the specific HT epitope. As one non-limiting example of how specific binding can be detected, once the test sample has been contacted with the antibodies bound to the solid support, a second, detectably-labeled antibody can be added, which recognizes a HT epitope distinct from the epitope recognized by the solid support-bound antibody.

A variety of other reagents may be included in the assays to detect HT polypeptides described herein. These include reagents such as salts, neutral proteins, e.g. albumin, detergents, etc., that are used to facilitate optimal protein-protein binding, and/or reduce non-specific or background interactions. Reagents that improve the efficiency of the assay, such as protease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-, vinca alkaloid, ricin A chain, methotrexate or radioactive isotope hapten).

Bispecific antibodies can be prepared as full length antibodies or antibody fragments (e.g. F (ab') 2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al, Nature, 305: 537-539 (1983)).

Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs-encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986). According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain (s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al, Science, 229: 81 (1985) describe a procedure wherein intact antibodies are proteolytically cleaved to generate F (ab') 2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F (ab') 2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148 (5): 1547-1553 (1992). The leucine zipper peptides from the Fos and Jun proteins were linked to the Fab portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al, Proc. Natl. Acad. Sci. USA, 90: 6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunology, 152: 5368 (1994). Antibodies with more than two valencies are also contemplated. For example, trispecific antibodies can be prepared. Tuttet al., J. Immunol. 147: 60 (1991).

Diagnostic Assays

The invention further provides methods for detecting the presence of and/or a level of HT mRNA in a biological sample; and methods for detecting the presence of and/or a level of HT polypeptide in a biological sample.

A particularly preferred embodiment involves the serial detection of each individual subunits in the sample in such a way that only HT molecules will be detected. This is done using a procedure which is an adaptation of how a standard ELISA works. In particular, an antibody to either APRIL or BLyS is immobilized (e.g., attached to a bead) and the sample is contacted to this antibody. Those molecules comprising the subunit for which the antibody is specific for will bind, while those homotrimers which do not include that subunit will be washed away. The bound molecules will then be put in contact with an detectable (labeled) antibody to the second subunit (e.g., biotinylated) and those molecules that were first captured that also include the second subunit (i.e., those molecules that are HT) will be detected. More specifically, if the first antibody is against APRIL, all homotrimeric BLyS molecules will be washed away in the first step. When these molecules are contacted with the second antibody that is specific for BLyS, all homotrimeric APRIL molecules will not bind and will be washed away. Thus, the remaining signal will be representative of the HT molecules (those comprising both BLyS and APRIL) in the sample. The known standard 2 APRIL/one BLyS HT molecule is used to construct a standard concentration curve, and the experimental signal obtained is compared to this standard curve to produce an estimated of the HT concentration in the biological sample.

In other embodiments, a method is provide for detecting a level of HT mRNA in a biological sample derived from an individual, comprising analyzing a polynucleotide sample from an individual for the level of HT polypeptide-encoding mRNA. The level of HT mRNA may be associated with autoimmune disease.

In still other embodiments, a method is provided for detecting the presence of and/or the level of a HT polypeptide in a biological sample.

A number of methods are available for determining the expression level of a HT nucleic acid molecule, e.g., a HT mRNA, or HT polypeptide in a particular sample. Diagnosis may be performed by a number of methods to determine the absence or presence or altered amounts of normal or abnormal HT mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a HT polypeptide may also be detected and/or quantitated in any way known to one of ordinary skill.

In addition, a test can include measurements of the expression of HT mRNA. Biochemical studies may be performed to determine whether a sequence polymorphism in a HT coding region or control regions is associated with disease. Disease associated polymorphisms may include deletion or truncation of the gene, mutations that alter expression level, that affect the activity of the protein, etc.

Changes in the promoter or enhancer sequence that may affect expression levels of HT can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Diagnostic methods of the subject invention in which the level of HT levels is of interest will typically involve comparison of the HT nucleic acid or protein abundance of a sample of interest with that of a control value to determine any relative differences, where the difference may be measured qualitatively and/or quantitatively, which differences are then related to the presence or absence of an abnormal HT levels. A variety of different methods for determine the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

By a gene whose expression level is "correlated with" or "associated with" a particular physiologic state, it is intended a gene whose expression shows a statistically significant correlation with the physiologic state. The strength of the correlation between the expression level of a differentially expressed gene and the presence or absence of a particular physiologic state may be determined by a statistical test of significance. Methods for determining the strength of a correlation between the expression level of a differentially-expressed gene and a particular physiologic state by assigning a statistical score to the correlation are reviewed in Holloway et al. (2002) *Nature Genetics Suppl.* 32:481-89, Churchill (2002) *Nature Genetics Suppl.* 32:490-95, Quackenbush (2002) *Nature Genetics Suppl.* 32: 496-501; Slonim (2002) *Nature Genetics Suppl.* 32:502-08; and Chuaqui et al. (2002) *Nature Genetics Suppl.* 32:509-514; each of which is herein incorporated by reference in its entirety. The statistical scores may be used to select the genes whose expression levels have the greatest correlation with a particular physiologic state in order to increase the diagnostic or prognostic accuracy of the methods of the invention.

Additional tests that have been associated with autoimmune disease severity or progression can be combined with the HT test described above to render a full diagnosis or outlook result.

For example, the American College of Rheumatology has developed 11 criteria to diagnose SLE, which span the clinical spectrum of SLE in aspects of skin, systemic, and laboratory tests. These criteria include malar rash, discoid rash, sensitivity to sun light, oral ulcers, arthritis, serositis, kidney and central nervous system inflammation, blood alterations, and the presence of antinuclear antibodies. A patient must meet four of these criteria in order to be classified as a SLE patient. (Tan et al. (1982) Arthritis Rheumatol. 25:1271-1277). SLE is usually confirmed by tests including, but not limited to, blood tests to detect anti-nuclear antibodies; blood and urine tests to assess kidney function; complement tests to detect the presence of low levels of complement that are often associated with SLE; a sedimentation rate (ESR) or C-reactive protein (CRP) to measure inflammation levels; X-rays to assess lung damage and EKGs to assess heart damage.

Monitoring Effects of Drug Treatment

Monitoring the influence of agents (e.g., drugs, compounds) on the levels of HT protein (e.g., modulation of transcriptional activation) can be applied not only in basic drug screening, but also in clinical trials. For example, the effectiveness of an agent determined by a screening assay as described herein to decrease HT protein levels, can be monitored in clinical trials of subjects exhibiting decreased HT gene expression or protein levels. In such clinical trials, the expression or activity of a HT gene, and preferably, other genes that have been implicated in, for example, a disorder associated with levels of HT protein can be used as a "read out" or markers of the phenotype of a particular cell, in the present case, B cells.

In some embodiments, the present invention provides a method for monitoring the effectiveness of treatment of a subject with an agent (e.g., an agonist, antagonist, peptidomimetic, protein, peptide, nucleic acid, small molecule, or other drug) comprising the steps of (i) obtaining a pre-administration sample from a subject prior to administration of the agent; (ii) detecting the level of expression of a HT protein or mRNA, in the pre-administration sample; (iii) obtaining one or more post-administration samples from the subject, (iv) detecting the level of expression or activity of the HT protein or mRNA in the post-administration samples; (v) comparing the level of expression or activity of the HT protein or mRNA in the pre-administration sample with the HT protein or mRNA in the post administration sample or samples; and (vi) altering the administration of the agent to the subject accordingly. According to such an embodiment, HT expression or activity may be used as an indicator of the effectiveness of an agent, even in the absence of an observable phenotypic response.

The basal expression level of HT in different tissue may be determined by analysis of tissue samples from individuals typed for the presence or absence of a specific polymorphism. Any convenient method may be use, e.g. ELISA, RIA, etc. for protein quantitation, northern blot or other hybridization analysis, quantitative RT-PCR, etc. for mRNA quantitation. The tissue specific expression is correlated with the genotype.

The alteration of HT expression in response to a modifier is determined by administering or combining the candidate modifier with an expression system, e.g. animal, cell, in vitro transcription assay, etc. The effect of the modifier on HT transcription and/or steady state mRNA levels is determined. As with the basal expression levels, tissue specific interactions are of interest. Correlations are made between the ability of an expression modifier to affect HT levels, and the presence of the provided polymorphisms. A panel of different modifiers, cell types, etc. may be screened in order to determine the effect under a number of different conditions.

Treatment Methods

The present invention provides a method of treating an individual clinically diagnosed with a condition associated with increased HT levels in serum. The methods generally comprises analyzing a biological sample to measure HT levels and comparing such levels to those present in healthy controls. A treatment plan that is most effective for individuals clinically diagnosed as having a condition associated with increased HT levels, such as autoimmune disease, is then selected and the patient is then treated accordingly. Thus, the invention further provides a method for predicting a patient's likelihood to respond to a drug treatment for a condition associated with increased HT levels, comprising determining a patient's expression of a HT gene, wherein the presence of a increased HT levels associated with an autoimmune condition, such as SLE, and is predictive of the patient's likelihood to respond to a drug treatment for the condition.

Thus, another aspect of the invention provides methods for tailoring an individual's therapeutic treatment with HT expression according to that individual's drug response. Pharmacogenomics allows a clinician or physician to target prophylactic or therapeutic treatments to patients who will most benefit from the treatment and to avoid treatment of patients who will experience toxic drug-related side effects.

Autoimmune Diseases

The following is a non-limiting list of the possible autoimmune diseases that treatment thereof could be aided by the use of the HT measuring assay presently disclosed. B-cell regulated autoimmune diseases include arthritis (rheumatoid arthritis, juvenile rheumatoid arthritis, osteoarthritis, psoriatic arthritis), psoriasis, dermatitis including atopic dermatitis; chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (including nephritis, non-renal, discoid, alopecia), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliaceus), autoimmune polyendocrinopathies, Reiter's disease, stiffman syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura(TTP), autoimmune thrombocytopenia, autoimmune disease of the testis and ovary including autoimune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre' Syndrome, Large Vessel Vasculitis (including Polymyalgia Rheumatica and Giant Cell (Takayasu's) Arteritis), Medium Vessel Vasculitis (includingKawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, and coronary artery disease.

BLyS and/or APRIL Antagonists

If high levels of HT in a patient suffering from an autoimmune disease are seen, this suggests the likelihood that the patient will response favorably to inhibition of BLyS and/or APRIL. Thus, the present invention also comprises BLyS and/or APRIL antagonists that are used for the treatment of autoimmune diseases wherein the patient has elevated levels of HT. The following are representative examples of BLyS and/or APRIL antagonists that could be utilized to treat such patients. For the purposes of functioning as a BLyS and/or APRIL antagonist, the extracellular domain of any of the TNFR family receptors is a polypeptide essentially free of the transmembrane or cytoplasmic domains that generally retains the ability to bind BLyS. Specifically, the extracellular domain of TACI can comprise amino acids 1 to 154 of the TACI polypeptide sequence (SEQ ID NO: 2). Additionally, the ECD can be fragments or variants of this sequence, such as ECD forms of TACI as described in von Bulow et al., supra, WO 98/39361, WO 00/40716, WO 01/85782, WO 01/87979, and WO 01/81417. In particular, these ECD forms can comprise amino acids 1-106 of SEQ ID NO:2, amino acids 1-142 of SEQ ID NO:2, amino acids 30-154 of SEQ ID NO:2, amino acids 30-106 of SEQ ID NO:2, amino acids 30-110 of SEQ ID NO:2, amino acids 30-119 of SEQ ID NO:2, amino acids 1-166 of SEQ ID NO:2, amino acids 1-165 of SEQ ID NO:2, amino acids 1-114 of SEQ ID NO: 2, amino acids 1-119 of SEQ ID NO:2, amino acids 1-120 of SEQ ID NO:2, and amino acids 1-126 of SEQ ID NO:2. In addition, the TACI ECD can comprise those molecules having only one cysteine rich domain ECD forms of BAFF-R include those comprising amino acids 1-71 of the BAFF-R polypeptide sequence (SEQ ID NO: 4). Additionally, the ECD can be fragments or variants of this sequence such as ECD forms of BAFF-R as described in WO 02/24909, WO 03/14294, and WO 02/38766. In particular, these ECD forms can comprise amino acids 1-77 of SEQ ID NO: 4, amino acids 7-77 of SEQ ID NO:4, amino acids 1-69 of SEQ ID NO:4, amino acids 7-69 of SEQ ID NO:4, amino acids 2-62 of SEQ ID NO:4, amino acids 2-71 of SEQ ID NO:4, amino acids 1-61 of SEQ ID NO:4 and amino acids 2-63 of SEQ ID NO:4, amino acids 1-45 of SEQ ID NO:4, amino acids 1-39 of SEQ ID NO:4, amino acids 7-39 of SEQ ID NO:4, amino acids 1-17 of SEQ ID NO:4, amino acids 39-64 of SEQ ID NO:4, amino acids 19-35 of SEQ ID NO:4, and amino acids 17-42 of SEQ ID NO:4. In addition, the BAFF-R ECD can comprise those molecules having a cysteine rich domain.

ECD forms of BCMA include those comprising amino acids 1-48 of the BCMA polypeptide sequence (SEQ ID NO: 6). Additionally, the ECD can be fragments or variants of this sequence, such as ECD forms of BCMA as described in WO 00/40716 and WO 05/075511. In particular, these ECD forms can comprise amino acids 1-150 of SEQ ID NO:6, amino acids 1-48 of SEQ ID NO:6, amino acids 1-41 of SEQ ID NO:6, amino acids 8-41 of SEQ ID NO:6, amino acids 8-37 of SEQ ID NO:6, amino acids 8-88 of SEQ ID NO:6, amino acids 41-88 of SEQ ID NO:6, amino acids 1-54 of SEQ ID NO:6, amino acids 4-55 of SEQ ID NO:6, amino acids 4-51 of SEQ ID NO:6, and amino acids 21-53 of SEQ ID NO:6. In addition, the BCMA ECD can comprise those molecules having only a partial cysteine rich domain.

In a further embodiment, the BLyS binding region of a BLyS receptor (e.g., an extracellular domain or fragment thereof of BAFF-R, BCMA or TACI) can be fused to an Fc portion of an immunoglobulin molecule to facilitate its solubility in vivo. According to one embodiment, the BLyS and/or APRIL antagonist binds to a BLyS polypeptide with a binding affinity of 100 nM or less. According to another embodiment, the BLyS and/or APRIL antagonist binds to a BLyS polypeptide with a binding affinity of 10 nM or less. According to yet another embodiment, the BLyS and/or APRIL antagonist binds to a BLyS polypeptide with a binding affinity of 1 nM or less.

In another example, BLyS and/or APRIL antagonists include BLyS binding polypeptides that are not native sequences or variants thereof. Some examples of such polypeptides are those having the sequence of Formula I, Formula II, Formula III as described in WO 05/000351. In particular, some binding polypeptides include ECFDLLVRAWVPCSVLK (SEQ ID NO:13), ECFDLLVRHWVPCGLLR (SEQ ID NO:14), ECFDLLVR-RWVPCEMLG (SEQ ID NO:15), ECFDLLVRSWVPCH-MLR (SEQ ID NO:16), ECFDLLVRHWVACGLLR (SEQ ID NO:17), or sequences listed in FIG. 32 of WO 05/000351.

Alternatively, the BLyS and/or APRIL antagonist can bind an extracellular domain of native sequence TACI, BAFF-R, or BCMA at its BLyS binding region to partially or fully block, inhibit or neutralize BLyS binding in vitro, in situ, or in vivo. For example, such indirect antagonist is a TACI antibody that binds in a region of TACI such that the binding of BLyS is sterically hindered. For example, binding at amino acids 72-109 or a neighboring region is believed to block BLyS binding. It could also be advantageous to block APRIL binding to this molecule, which is believed to occur in the region of amino acids 82-222. Another BLyS and/or APRIL antagonist is a BAFF-R antibody that binds in a region of BAFF-R such that binding of human BAFF-R to BLyS is sterically hindered. For example, binding at amino acids 23-38 or amino acids 17-42 or a neighboring region is believed to block BLyS binding. Finally, a further indirect antagonist would be a APRIL antibody that binds in a region of APRIL such that the binding of BLyS is sterically hindered. For example, binding at amino acids 5-43 or a neighboring region is believed to block BLyS (or APRIL) binding.

In some embodiments, a BLyS and/or APRIL antagonist according to this invention includes BLyS antibodies. The term "antibody" when referring to is used in the broadest sense and specifically covers, for example, monoclonal antibodies, polyclonal antibodies, antibodies with polyepitopic specificity, single chain antibodies, and fragments of antibodies. According to some embodiments, a polypeptide of this invention is fused into an antibody framework, for example, in the variable region or in a CDR such that the antibody can bind to and inhibit BLyS binding to TALI, BAFF-R, or BCMA or inhibits BLyS signaling. The antibodies comprising a polypeptide of this invention can be chimeric, humanized, or human. The antibodies comprising a polypeptide of this invention can be an antibody fragment. Alternatively, an antibody of this invention can be produced by immunizing an animal with a polypeptide of this invention. Thus, an antibody directed against a polypeptide of this invention is contemplated.

In particular, antibodies specific for BLyS that bind within a region of human BLyS (SEQ ID NO: 8) comprising residues 162-275 and/or a neighboring amino acid of amino acids selected from the group consisting of 162, 163, 206, 211, 231, 233, 264 and 265 of human BLyS are contemplated. The binding of the antibodies are such that the antibody sterically hinders BLyS binding to one or more of its receptors. Such antibodies are described in WO 02/02641 and WO 03/055979. A particularly preferred antibody is the one described as Lymphostat-B (Baker et al. (2003) Arthritis Rheum, 48, 3253-3265).

Other Immunosuppressive Drugs

The present method contemplates the use of other immunosuppressive drugs either singly or in combination with a BLyS and/or APRIL inhibitor. These other drugs include, but are not limited to, immunosuppressive agents such as calcineurin inhibitors (e.g., cyclosporin A or FK506), steroids (e.g., methyl prednisone or prednisone), or immunosuppressive agents that arrest the growth of immune cells (e.g., rapamycin), anti-CD40 pathway inhibitors (e.g., anti-CD40 antibodies, anti-CD40 ligand antibodies and small molecule inhibitors of the CD40 pathway), transplant salvage pathway inhibitors (e.g., mycophenolate mofetil (MMF)), IL-2 receptor antagonists (e.g., Zeonpax.COPYRGT. from Hoffmann-la Roche Inc., and Simulet from Novartis, Inc.), or analogs thereof, cyclophosphamide, thalidomide, azathioprine, monoclonal antibodies (e.g., Daclizumab (anti-interleukin (IL)-2), Infliximab (anti-tumor necrosis factor), MEDI-205 (anti-CD2), abx-cbl (anti-CD147)), and polyclonal antibodies (e.g., ATG (anti-thymocyte globulin)).

Pharmaceutical Formulations

Therapeutic formulations of the BLyS and/or APRIL antagonists such as BLyS-binding antibodies used in accordance with the present invention are prepared for storage by mixing an antibody having the desired degree of purity with optional pharmaceutically acceptable carriers, excipients or stabilizers (Remitgtorz's Pharmaceutical Science 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN, PLURONICS™ or polyethylene glycol (PEG)).

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly (2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT (injectablemicrospheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Assay to Measure HT Levels

Reagents: Anti-APRIL antibody conjugated to bead (ex. ZGEN anti-APRIL antibody E9617 (clone 319.6.8.5) conjugated to BioRad xMap bead 106 (Hercules, Calif.))
Anti-BLyS antibody biotinylated (ZGEN anti-BLyS antibody E4731 (clone 258.2.1.9.1.3) biotinylated)
Streptavidin-PE (Jackson ImmunoResearch. Labs, Inc (West Grove, Pa.) #016-110-084)
Multiscreen plates (Millipore (Billerica, Mass.), MABVN1250) ELISA B (ELISA C+1% BSA+NaAz)
APRIL/BLyS Heterotrimer LOT A 1642F Standard (25 ng/mL), QC1 (7.5 ng/mL), and QC2 (500 pg/mL) (2 APRIL subunits, one BLyS) Samples
Human AB Serum (prescreened for low BLyS and APRIL content) Shaker
1) Bring all reagents to room temperature
2) Block plate: add 100 uL of ELISA B to all wells, shake for 10', vacuum.
3) Vortex beads 30", sonicate beads 30"
   a. Determine volume of beads to add: 5K beads/well in 25 uL/well ELISA B
   b. For one full plate 2.5 mL+5E5 beads
4) Add 25 uL bead mixture per well to all wells.
5) Dilute standards: Dilute A1642F standard (25 ng/mL) in ELISA B, 1:3 six times for an 7 point dilution series: 25000, 8333, 2778, 926, 309, 103, and 34 pg/mL.
6) Add 25 uL 25000 pg/mL standard to A1, 8333 pg/mL standard to B1, etc.
7) Add 25 uL QC1 to A2, add 25 uL QC2 to B2.
8) Add 25 uL serum to all standard, background, and QC wells.
9) Add 25 uL ELISA B to all sample wells and the background well.
10) Add 25 uL serum sample to each sample well *, **.
11) Seal plate and cover in foil. Place on shaker at 600 RPM for 60' at RT.
12) Vacuum. Wash plate with 2×100 uL ELISA B.
13) Add 25 uL/well of 1ug/mL antibody E4731-biotin.
14) Seal plate and cover in foil. Place on shaker at 600 RPM for 60'
15) Without washing or vacuuming add 25 uL/well 1:100 SA-PE in ELISA B.
16) Seal plate and cover in foil. Place on shaker at 600 RPM for 30'
17) Vacuum. Wash plate with 2×100 uL ELISA B.
18) Add 110 uL ELISA B per well. Mix at 600 RPM for 5'
19) Run on Luminex 100.

Plate Map

|   | 1 | 2 | 3 | 4 | 5 | 6 | 7 | 8 | 9 | 10 | 11 | 12 |
|---|---|---|---|---|---|---|---|---|---|----|----|----|
| A | 25000 | QC1 | S2 | S4 | S6 | S8 | S10 | S12 | S14 | S16 | S18 | S20 |
| B | 8333 | QC2 | 1:4 | 1:4 | 1:4 | 1:4 | 1:4 | 1:4 | 1:4 | 1:4 | 1:4 | 1:4 |
| C | 2778 |  | 1:8 | 1:8 | 1:8 | 1:8 | 1:8 | 1:8 | 1:8 | 1:8 | 1:8 | 1:8 |
| D | 926 |  | 1:16 | 1:16 | 1:16 | 1:16 | 1:16 | 1:16 | 1:16 | 1:16 | 1:16 | 1:16 |
| E | 309 | S1 | S3 | S5 | S7 | S9 | S11 | S13 | S15 | S17 | S19 | S21 |
| F | 103 | 1:4 | 1:4 | 1:4 | 1:4 | 1:4 | 1:4 | 1:4 | 1:4 | 1:4 | 1:4 | 1:4 |
| G | 34 | 1:8 | 1:8 | 1:8 | 1:8 | 1:8 | 1:8 | 1:8 | 1:8 | 1:8 | 1:8 | 1:8 |
| H | B | 1:16 | 1:16 | 1:16 | 1:16 | 1:16 | 1:16 | 1:16 | 1:16 | 1:16 | 1:16 | 1:16 |

It is very important to run samples neat and at the following dilutions: 1:4, 1:8, and 1:16. This is necessary to allow native HT complexes to dissociate, and this is not a serum effect. Serum concentration must be kept constant throughout the dilution series by diluting samples with the serum standard. Having less than 25 uL serum in each well can cause those wells to exhibit erroneous values.

Example of Assay Performance:

|  | Heterotrimer pg/mL | | Statistics | |
|---|---|---|---|---|
|  | Expected | Observed | % CV | Relative Error |
| Standards | 25000 | 27062 | 2.0% | −8.2% |
|  | 8333 | 8039 | 0.4% | 3.5% |
|  | 2778 | 2931 | 3.0% | −5.5% |
|  | 926 | 874 | 3.6% | 5.6% |
|  | 309 | 316 | 1.4% | −2.5% |
|  | 103 | 110 | 13.0% | −7.2% |
|  | 34 | 32 | 13.9% | 7.3% |
| QC1 | 7500 | 7259 | 12.3% | 3.2% |
| QC2 | 500 | 455 | 5.5% | 8.9% |

Acceptable values for the standard and quality controls are +/−25% of expected values. The assay LOD is expected to be 100 pg/mL with samples run neat (100% serum). The assay may run accurately down to 34 pg/mL.

The standard used in this assay is a HT containing 2 APRIL subunits and 1 BLyS subunit. The absolute values of native HT will be different if this molecule is relatively uncommon in patient serum, however, at this time there is evidence that there is any bias for any particular trimeric combination.

Example 2

Measurement of HT in Patient and Healthy Control Sera

Figure 2:
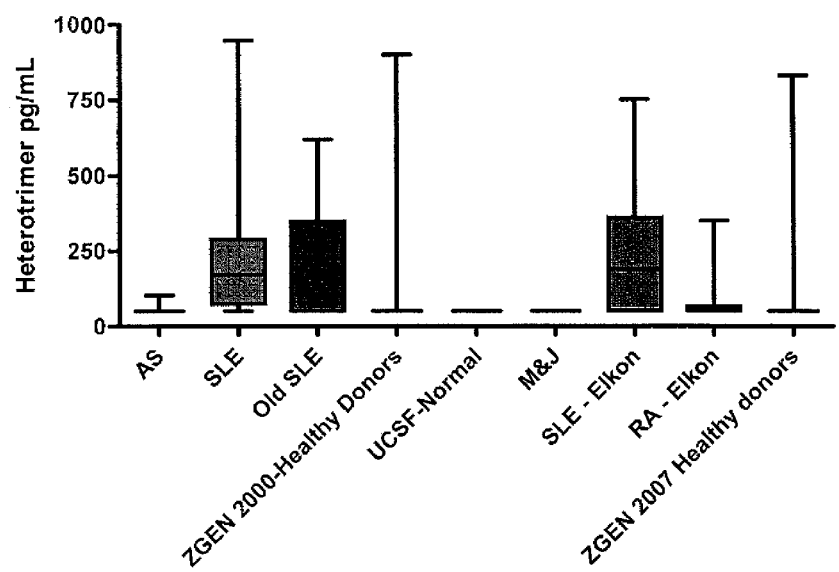
FIG. 2 expresses the data of FIG. 1 showing average heterotrimer levels.
Figure 3:
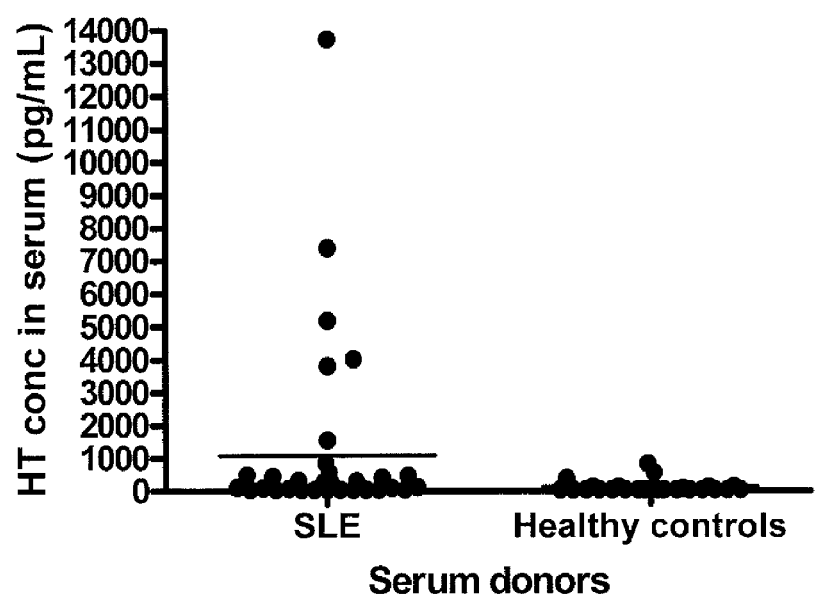
FIG. 3 graphs the heterotrimer levels of a second cohort of SLE patients.

ZymoZipper N-terminal trimerization domain enabled production of recombinant BLyS/APRIL heterotrimers (rHT), which were used as a standard to develop a bead-based immunoassay to quantitate native HT in human serum as described in Example 1. This assay, along with BLyS- and APRIL-specific ELISAs were used to measure these 3 ligands in sera from healthy controls (HC; n=79) and from systemic lupus erythematosus (SLE; n=30) and rheumatoid arthritis (RA; n=29) patients (see FIGS. 1 and 2). Biological activity of rHT was compared with that of rBLyS and rAPRIL in a 4-hr signaling assay using TACI-transfected Jurkat cells with a NFκB/luciferase reporter gene, and in a 4-day primary human B cell proliferation assay.

Significantly more SLE patients than HC had detectable HT in serum (70% vs. 14%, p<0.0001, Fisher's exact test), and 24% of RA patients had detectable HT. In this cohort, mean serum HT levels were 177 pg/mL (SLE), 64 pg/mL (RA), and 66 pg/mL (HC). In the TACI-Jurkat assay (see Example 4), rHT signaling is similar to that of BLyS or APRIL. In the B cell assay (see Example 3), rHT are less potent inducers than the homotrimeric ligands (EC50 values: 0.02 nM for BLyS, 0.17 nM for APRIL and 4.06 nM for HT). This likely reflects the predominant expression of BAFF-R, to which our rHT bind poorly, on circulating B cells. Atacicept and BCMA-Ig neutralize the activity of all 3 ligands in these assays, while BAFFR-Ig exhibits little to no inhibition of rHT activity. Our data confirm that native HT are elevated in autoimmune patients, and demonstrate that rHT are biologically active. Whether native HT have a biological role distinct from their homotrimeric counterparts remains to be determined. Atacicept inhibits the bioactivity of all 3 ligand forms, which may prove important in the clinical treatment of autoimmune disease.

In a second set of SLE patients, including 72 SLE patients and 42 healthy controls. BLyS and APRIL levels were determined by ELISA. HT levels were measured in 36 patients and 25 controls using a luminex-based assay. HT were detected in more patients than controls (72% vs. 32% $\chi^2$=0.0019).

Example 3

B-Cell Proliferation Assay

A vial containing 1×108 frozen, apheresed peripheral blood mononuclear cells (PBMCs) was quickly thawed in 370C water bath and resuspended in 25 ml B cell medium (RPMI-1640 Medium, 10% heat inactivated fetal bovine serum, 5% L-glutamine, 5% Pen/Strep) in a 50 ml tube. Cells were tested for viability using Trypan Blue (GIBCO BRL, Gaithersburg, Md.). CD19+ B cells were then isolated by positive selection using anti-CD 19 coated microbeads (Miltenyi Biotech). Coated cells were then isolated on a MACS LS column (Miltenyi Biotech) The B cells were resuspended at a final concentration of 1.6×10 cells/ml in B cell medium and plated at 100 µl/well in a 96 well U bottom plate (Falcon, VWR, Seattle, Wash.). HT and homotrimeric ligands were prepared and were added to the cells in 3 fold dilutions from 1000 ng/ml to 0 ng/ml. Final volume was 200 µl/well.

The cells were then incubated at 370C in a humidified incubator for 72 hours. Sixteen hours prior to harvesting, 1 µCi 3H thymidine was added to all wells. The cells were harvested into a 96 well filter plate (UniFilter GF/C, Packard, Meriden, Conn.) where they were harvested using a cell harvester (Packard) and collected according to manufacturer's instructions. The plates were dried at 55° C. for 20-30 minutes and the bottom of the wells were sealed with an opaque plate sealer. To each well was added 0.25 ml of scintillation fluid (Microscint-O, Packard) and the plate was read using a TopCount Microplate Scintillation Counter (Packard).

Example 4

TACI Transfected Jurkat Cell Bioassay

The TACI in vitro bioassay uses a Jurkat cell line (human acute T cell lymphocyte, KZ142, clone #24) that has been transfected with two plasmids. First, the cell line was transfected with a plasmid containing a luciferase reporter gene under control of the NF-κβ/AP-1 promoter and a neomycin-resistance gene. An appropriate clone was chosen after G418 selection. This cell line was then transfected with a plasmid containing the full length TACI cDNA under control of the CMV promoter (TACI/pZP7P) and a puromycin-resistent gene. Clones were selected with puromycin and then an appropriate cell line chosen for the assay by assessing for TACI expression by flow cytometry using TACI monoclonal antibodies.

The assay is based on recording the readout of the luciferase gene expression that is triggered by the binding of the test ligand (HT or homotrimeric BLyS or homotrimeric APRIL) to cell surface TACI produced by from the TACI cDNA.

The transfected Jurkat cells were propagated in RPMI 1640 media without phenol red (Rosewell Park Memorial Institute, Buffalo, N.Y.) with 10% FBS added. Puromycin was added at 2 µg/ml as a selective reagent for the transfection. Sodium pyruvate and L-glutamine were also added to the media at 1% volume. Steady-Glo Luciferase Assay System (Promega, Madison, Wis. #E2510) substrate and assay buffer were used according to manufacturer's instructions.

The assay was performed by resuspending transfected Jurkat cells in media to 1.6×106 cell/ml. Cells are plated on a white assay plate with 50λ\ per well. Samples of ZZ-APRIL were brought to appropriate dilution and placed into a 96 well plate. Dilutions were added to the cells, at 50µλ per well. The plate was included 4 hrs in a 37° incubator. During incubation, the Steady-GLO buffer and substrate was equilibrated to room temperature. After the 4 hr. incubation, the plate was allowed to cool at room temperature for 5 minutes. Assay buffer and substrate were mixed together and added at 100 µl per well. The plates were vortexed at low setting for 1 minute to mix, then incubated at room temperature for 10 minutes. The plate was then read on a luminometer with 5 second integration.

That which is claimed:

1. A method of treating an individual with systemic lupus erythematosus (SLE) comprising:
   (a) detecting native BLyS/APRIL heterotrimer (HT) protein levels of the individual comprising measuring a first level of native HT protein in a serum sample from said individual wherein measuring utilizes a bead-based immunoassay employing an anti-APRIL antibody and an anti-BLyS antibody;
   (b) comparing said first native HT protein level to a second native HT protein level in a serum sample of a healthy individual;
   (c) determining whether said first native HT protein level is increased as compared to said second native HT protein level, wherein said increased first native HT protein level is associated with SLE; and wherein said native HT protein causes proliferation of B cells and production of immunoglobulin in an in vitro assay;
   (d) selecting a treatment plan for individuals with SLE and having an increase in HT levels; and,
   (e) administering said treatment plan to said individual, wherein said treatment plan comprises administration of an HT antagonist.

2. The method of claim 1, wherein said HT antagonist is also a BLyS antagonist.

3. The method of claim 1, wherein said HT antagonist is also an APRIL antagonist.

4. The method of claim 1, wherein said bead-based immunoassay utilizes anti-APRIL antibody conjugated to beads and a detectable anti-BLyS antibody.

5. The method of claim 4, wherein said bead-based immunoassay utilizes anti-APRIL antibody conjugated to beads and a biotinylated anti-BLyS antibody.

6. A method for predicting an individual's likelihood to respond to a drug treatment for systemic lupus erythematosus (SLE) comprising:
   (a) detecting native BLyS/APRIL heterotrimer (HT) protein levels of the individual comprising measuring a first level of native HT protein in a serum sample from said individual wherein measuring utilizes a bead-based immunoassay employing an anti-APRIL antibody and an anti-BLyS antibody;
   (b) comparing said first native HT protein level to a second native HT protein level in a serum sample of a healthy individual;
   (c) determining whether said first native HT protein level is increased as compared to said second native HT protein level, wherein said increased first native HT protein level is associated with SLE and is predictive that said individual will successfully respond to a treatment plan that neutralizes B cells; and wherein said native HT protein causes proliferation of B cells and production of immunoglobulin in an in vitro assay;
   (d) selecting a treatment plan for individuals with SLE and having an increase in HT levels; and,
   (e) administering said treatment plan to said individual, wherein said treatment plan comprises administration of an HT antagonist.

7. The method of claim 6, wherein said HT antagonist is also a BLyS antagonist.

8. The method of claim 6, wherein said HT antagonist is also an APRIL antagonist.

9. The method of claim 6, wherein said bead-based immunoassay utilizes anti-APRIL antibody conjugated to beads and a detectable anti-BLyS antibody.

10. The method of claim 9, wherein said bead-based immunoassay utilizes anti-APRIL antibody conjugated to beads and a biotinylated anti-BLyS antibody.

* * * * *

UNITED STATES PATENT AND TRADEMARK OFFICE
CERTIFICATE OF CORRECTION

PATENT NO. : 9,146,242 B2
APPLICATION NO. : 13/972186
DATED : September 29, 2015
INVENTOR(S) : Stacey Dillon et al.

Page 1 of 1

It is certified that error appears in the above-identified patent and that said Letters Patent is hereby corrected as shown below:

On the Title Page:

OTHER PUBLICATIONS:

Column 2, line 27, Johnson, Marlin et al. reference:

Delete "Sjö gren's" and insert -- Sjögren's --, therefor.

Column 2, line 40, Rutgers University reference:

Delete "websit" and insert -- website --, therefor.

Signed and Sealed this
Fifth Day of July, 2016

Michelle K. Lee
*Director of the United States Patent and Trademark Office*